US011883099B2

(12) United States Patent
Jia et al.

(10) Patent No.: US 11,883,099 B2
(45) Date of Patent: Jan. 30, 2024

(54) NONINVASIVE TECHNIQUES FOR IDENTIFYING CHOROIDAL NEOVASCULARIZATION IN RETINAL SCANS

(71) Applicant: Oregon Health & Science University, Portland, OR (US)

(72) Inventors: Yali Jia, Portland, OR (US); Jie Wang, Portland, OR (US)

(73) Assignee: Oregon Health & Science University, Portland, OR (US)

(*) Notice: Subject to any disclaimer, the term of this patent is extended or adjusted under 35 U.S.C. 154(b) by 584 days.

(21) Appl. No.: 16/952,619

(22) Filed: Nov. 19, 2020

(65) Prior Publication Data
US 2021/0153738 A1  May 27, 2021

Related U.S. Application Data

(60) Provisional application No. 63/006,015, filed on Apr. 6, 2020, provisional application No. 62/941,499, filed on Nov. 27, 2019.

(51) Int. Cl.
| | | |
|---|---|---|
| A61B 3/10 | (2006.01) | |
| A61B 3/12 | (2006.01) | |
| A61B 3/00 | (2006.01) | |
| G06T 7/62 | (2017.01) | |

(52) U.S. Cl.
CPC .......... *A61B 3/102* (2013.01); *A61B 3/0025* (2013.01); *A61B 3/0058* (2013.01); *A61B 3/1241* (2013.01); *G06T 7/62* (2017.01); *G06T 2207/10101* (2013.01); *G06T 2207/20024* (2013.01); *G06T 2207/20076* (2013.01);
(Continued)

(58) Field of Classification Search
CPC ..... A61B 3/102; A61B 3/0025; A61B 3/0058; A61B 3/1241; A61B 3/1233; G06T 7/62; G06T 2207/10101; G06T 2207/20024; G06T 2207/20076; G06T 2207/20081; G06T 2207/20084; G06T 2207/30041; G06T 2207/30101; G06T 7/11
See application file for complete search history.

(56) References Cited

U.S. PATENT DOCUMENTS

2013/0165771 A1* 6/2013 Ni ...................... A61K 49/0043
                                                                600/431

OTHER PUBLICATIONS

Al-Sheikh, et al., "Biomarkers of Neovascular Activity in Age-Related Macular Degeneration Using Optical Coherence Tomography (OCT) Angiography," Retina, vol. 38, No. 2, Feb. 2018, pp. 220-230.

(Continued)

*Primary Examiner* — James C. Jones
(74) *Attorney, Agent, or Firm* — Katherine M. Mead; Tanya M. Harding; Lee & Hayes, P.C.

(57) ABSTRACT

Methods and systems for identifying CNV membranes and vasculature in images obtained using noninvasive imaging techniques are described. An example method includes generating, by a first model based on at least one image of a retina of a subject, a membrane mask indicating a location of a CNV membrane in the retina. The method further includes generating, by a second model based on the membrane mask and the at least one image, a vasculature mask of the retina of the subject, the vasculature mask indicating CNV vascularization in the retina.

20 Claims, 23 Drawing Sheets
(15 of 23 Drawing Sheet(s) Filed in Color)

(52) U.S. Cl.
CPC ............. *G06T 2207/20081* (2013.01); *G06T 2207/20084* (2013.01); *G06T 2207/30041* (2013.01)

(56) References Cited

OTHER PUBLICATIONS

Bailey, et al., "Detection of Non-exudative Choroidal Neovascularization and Progression to Exudative Choroidal Neovascularization Using Optical Coherence Tomography Angiography," Ophthalmology Retina, vol. 3, No. 8, Aug. 2019, 15 pages.
Bhavsar, et al., "Projection-resolved optical coherence tomography angiography exhibiting early flow prior to clinically observed retinal angiomatous proliferation," American Journal of Ophthalmology Case Reports, vol. 8, Dec. 2017, pp. 53-57.
Bonini Filho, et al., "Association of Choroidal Neovascularization and Central Serous Chorioretinopathy With Optical Coherence Tomography Angiography," JAMA Ophthalmology, vol. 133, No. 8, May 2015, pp. 899-906.
Camino, et al., "Deep learning for the segmentation of preserved photoreceptors on en face optical coherence tomography in two inherited retinal diseases," Biomedical Optics Express, vol. 9, No. 7, Jul. 2018, pp. 3092-3105.
Chen, et al., "DeepLab: Semantic Image Segmentation with Deep Convolutional Nets, Atrous Convolution, and Fully Connected CRFs," IEEE Transactions on Pattern Analysis and Machine Intelligence, vol. 40, No. 4, Apr. 2018, pp. 834-848.
Chen, et al., "Rethinking Atrous Convolution for Semantic Image Segmentation," arXiv, Dec. 2017, 14 pages.
Congdon, et al., "Causes and prevalence of visual impairment among adults in the United States," Archives of Ophthalmology, Arch Ophthalmology, vol. 122, No. 4, Apr. 2004, pp. 477-485.
De Jong, "Age-Related Macular Degeneration," The New England Journal of Medicine, vol. 355, No. 14, Oct. 2006, pp. 1474-1485.
Donoso, et al., "The Role of Inflammation in the Pathogenesis of Age-related Macular Degeneration," Survey of Ophthalmology, vol. 51, No. 2, Ma.-Apr. 2006, pp. 137-152.
Friedman, et al., "Prevalence of Age-Related Macular Degeneration in the United States," Archives of Ophthalmology, vol. 122, No. 4, Apr. 2004, pp. 564-572.
Grossniklaus, et al., "Choroidal Neovascularization," Perspective, American Journal of Ophthalmology, vol. 137, No. 3, Mar. 2004, pp. 496-503.
Guo, et al., "Automated segmentation of retinal layer boundaries and capillary plexuses in wide-field optical coherence tomographic angiography," Biomedical Optics Express, vol. 9, No. 9, Sep. 2018, pp. 4429-4442.
Hee, et al., "Optical Coherence Tomography of Age-related Macular Degeneration and Choroidal Neovascularization," Ophthalmology, vol. 103, No. 8, Aug. 1996, pp. 1260-1270.
Huang, et al., "Densely Connected Convolutional Networks," Proceedings of the IEEE Conference on Computer Vision and Pattern Recognition, Jul. 2017, pp. 4700-4708.
Inoue, et al., "Optical Coherence Tomography Angiography of Polypoidal Choroidal Vasculopathy and Polypoidal Choroidal Neovascularization," Retina, The Journal of Retinal and Vitreous Diseases, vol. 35, No. 11, Nov. 2015, pp. 2265-2274.
Jager, et al., "Age-Related Macular Degeneration," The New England Journal of Medicine, vol. 358, No. 24, Jun. 2008, pp. 2606-2617.
Jia, et al., "Split-spectrum amplitude-decorrelation angiography with optical coherence tomography," Optics Express, vol. 20, No. 4, Feb. 2012, pp. 4710-4725.
Jia, et al., "Quantitative Optical Coherence Tomography Angiography of Choroidal Neovascularization in Age-Related Macular Degeneration," Ophthalmology, vol. 121, No. 7, Jul. 2014, pp. 1435-1444.
Jia, et al., "Quantitative optical coherence tomography angiography of vascular abnormalities in the living human eye," PNAS USA, vol. 112, No. 18, Apr. 2015, pp. 2395-2402.
Kuehlewein, et al., "Optical Coherence Tomography Angiography of Type 1 Neovascularization in Age-Related Macular Degeneration," American Journal of Ophthalmology, vol. 160, No. 4, Oct. 2015, pp. 739-748.E2.
Liu, et al., "Automated choroidal neovascularization detection algorithm for optical coherence tomography angiography," Biomedical Optics Express, vol. 6, No. 9, Aug. 2015, pp. 3564-3575.
Lopez-Saez, et al., "Fluorescein-Induced Allergic Reaction," Annals of Allergy, Asthma & Immunology, vol. 81, No. 5, Nov. 1998, pp. 428-430.
Nesper, et al., "vol. Rendered Projection-Resolved OCT Angiography: 3D Lesion Complexity is Associated With Therapy Response in Wet Age-Related Macular Degeneration," Investigative Ophthalmology & Visual Science, vol. 69, No. 5, Apr. 2018, pp. 1944-1952.
Otsu, "A Threshold Selection Method from Gray-Level Histograms," IEEE Transactions on Systems, Man, and Cybernetics, vol. 9, No. 1, Jan. 1979, pp. 62-66.
Patel, et al., "Classification of Choroidal Neovascularization Using Projection-Resolved Optical Coherence Tomographic Angiography," Investigative Ophthalmology & Visual Science, vol. 59, No. 10, Aug. 2018, pp. 4285-4291.
Patel, et al., "Plexus-Specific Detection of Retinal Vascular Pathologic Conditions with Projection-Resolved OCT Angiography," Ophthalmology Retina, vol. 2, No. 8, Aug. 2018, pp. 816-826.
Spaide, et al., "Image Artifacts in Optical Coherence Tomography Angiography," Retina, vol. 35, No. 11, Nov. 2015, pp. 2163-2180.
Stanga, et al., "Indocyanine Green Angiography in Chorioretinal Diseases: Indications and Interpretation: An Evidence-based Update," Ophthalmology, vol. 110, No. 1, Jan. 2003, pp. 15-21.
Treister, et al., "Prevalence of Subclinical CNV and Choriocapillaris Nonperfusion in Fellow Eyes of Unilateral Exudative AMD on OCT Angiography," Translational Vision Science & Technology, vol. 7, No. 5, Oct. 2018, 10 pages.
Wang, et al., "Automated diagnosis and segmentation of choroidal neovascularization in OCT angiography using deep learning," Biomedical Optics Express, vol. 11, No. 2, Feb. 2020, pp. 927-944.
Wang, et al., "Reflectance-based projection-resolved optical coherence tomography angiography [Invited]," Biomedical Optics Express, vol. 8, No. 3, Mar. 2017, pp. 1536-1548.
Wei, et al., "Fast and robust standard deviation-based method for bulk motion compensation in phase-based functional OCT," Optics Letters, vol. 43, No. 9, May 2018, pp. 2204-2207.
Xue, et al., "Automatic quantification of choroidal neovascularization lesion area on OCT angiography based on density cell-like P systems with active membranes," Biomedical Optical Express, vol. 9, No. 7, Jul. 2018, pp. 3208-3219.
Zang, et al., "Automated segmentation of peripapillary retinal boundaries in OCT combining a convolutional neural network and a multi-weights graph search," Biomedical Optics Express, vol. 10, No. 8, Aug. 2019, pp. 4340-4352.
Zhang, et al., "Advanced image processing for optical coherence tomographic angiography of macular diseases," Biomedical Optics Express, vol. 6, No. 12, Nov. 2015, pp. 4661-4675.
Zhang, et al., "Automated Quantitation of Choroidal Neovascularization: A Comparison Study Between Spectral-Domain and Swept-Source OCT Angiograms," Investigative Ophthalmology & Visual Science, vol. 58, No. 3, Mar. 2017, pp. 1506-1513.
Zhang, et al., "Minimizing projection artifacts for accurate presentation of choroidal neovascularization in OCT micro-angiography," Biomedical Optics Express, vol. 6, No. 10, Oct. 2015, pp. 4130-4143.
Zhang, et al., "Projection-resolved optical coherence tomographic angiography," Biomedical Optics Express, vol. 7, No. 3, Mar. 2016, pp. 816-828.

\* cited by examiner

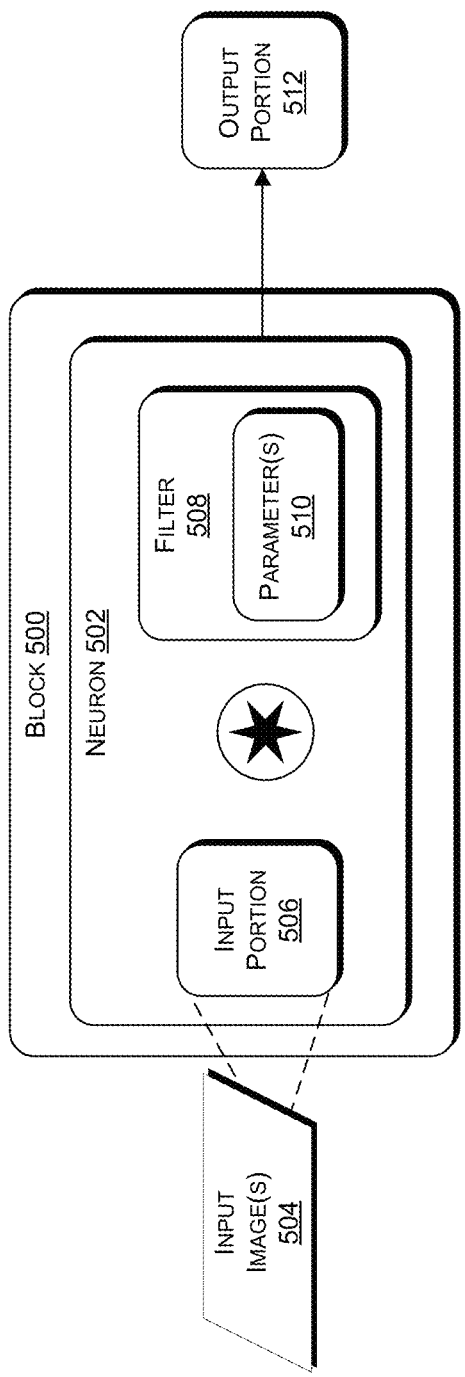

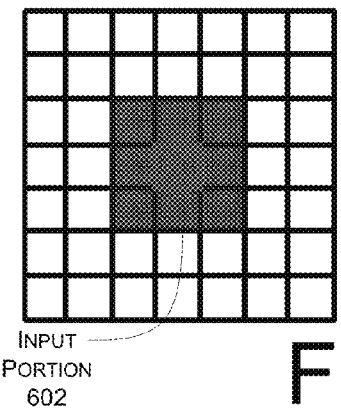  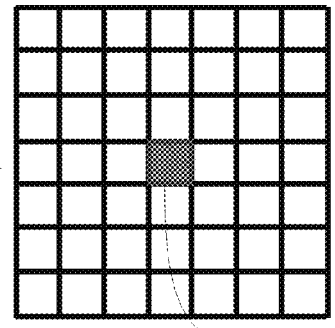
INPUT PORTION 602     FIG. 6A     OUTPUT PORTION 604
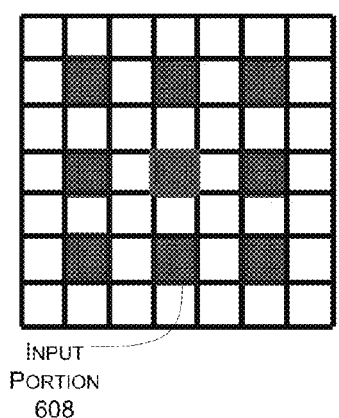  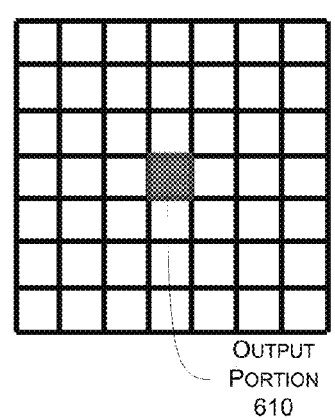
INPUT PORTION 608     FIG. 6B     OUTPUT PORTION 610
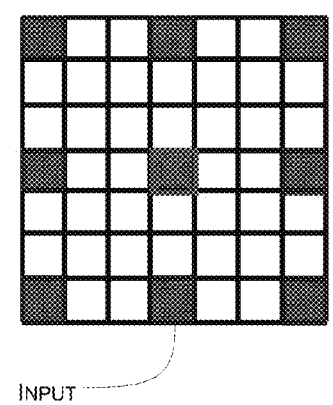  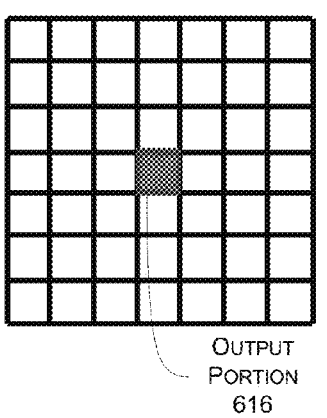
INPUT PORTION 614     FIG. 6C     OUTPUT PORTION 616

NONINVASIVE TECHNIQUES FOR IDENTIFYING CHOROIDAL NEOVASCULARIZATION IN RETINAL SCANS

CROSS-REFERENCE TO RELATED APPLICATIONS

This application claims the priority of U.S. Provisional Application No. 62/941,499, which was filed on Nov. 27, 2019, and U.S. Provisional Application No. 63/006,015, which was filed on Apr. 6, 2020, each of which is incorporated by reference herein in its entirety.

STATEMENT REGARDING FEDERALLY SPONSORED RESEARCH

This invention was made with government support under grants EY024544, EY027833, and EY010572 awarded by the National Institutes of Health. The government has certain rights in the invention.

TECHNICAL FIELD

This disclosure relates generally to systems, devices, and methods for identifying and monitoring choroidal neovascularization (CNV) in subjects using noninvasive imaging techniques, such as optical coherence tomographic angiography (OCTA).

BACKGROUND

Age related macular degeneration (AMD) is a leading cause of vision loss and irreversible blindness (N. Congdon et al., ARCHIVES OF OPHTHALMOLOGY 122, 477-485 (2004); D. S. Friedman et al., ARCHIVES OF OPHTHALMOLOGY 122, 564-572 (2004); R. D. Jager et al., NEJM 358, 2606-2617 (2008)). AMD is characterized as neovascular based on the presence of CNV, a pathological condition in which new vessels grow from the choroid into the outer retina (R. D. Jager et al., NEJM 358, 2606-2617 (2008); H. E. Grossniklaus et al., AMERICAN JOURNAL OF OPHTHALMOLOGY 137, 496-503 (2004); P. T. DeJong, NEJM 355, 1474-1485 (2006); M. R. Hee et al., OPHTHALMOLOGY 103, 1260-1270 (1996)). CNV can cause vision loss because CNV can result in subretinal hemorrhage, lipid exudation, subretinal fluid, intraretinal fluid, or formation of fibrotic scars (L. A. Donoso et al., SURVEY OF OPHTHALMOLOGY 51, 137-152 (2006); P. E. Stanga et al., OPHTHALMOLOGY 110, 15-21 (2003)). Dye-based angiography techniques, such as techniques using fluorescein (FA) and indocyanine green angiography (ICGA), are traditionally used for CNV identification and visualization.

Optical coherence tomographic angiography (OCTA), can measure flow signal in vivo by evaluating motion contrast between subsequent OCT B-scans at the same location (Y. Jia et al., OPTICS EXPRESS 20, 4710-4725 (2012); R. F. Spade et al., Retina 35, 2163 (2015)). In contrast to conventional dye-based imaging modalities, OCTA is non-invasive, has rapid acquisition, is high-resolution, and generates three-dimensional data sets. Recently, projection-resolved (PR) OCTA has proven adept at removing projection artifacts, and consequently shown diagnostic potential and enabled detailed quantification of CNV (J. Wang et al., BIOMEDICAL OPTICS EXPRESS 8, 1536-1538 (2017); M. Zhang et al., BIOMEDICAL OPTICS EXPRESS 7, 816-828 (2016); R. C. Patel et al., RETINA 2, 816-826 (2018); R. Patel et al., INVESTIGATIVE OPHTHALMOLOGY & VISUAL SCIENCE 59, 4285-4291 (2018); K. V. Bhaysar et al., AMERICAN JOURNAL OF OPHTHALMOLOGY CASE REPORTS 8, 53-57 (2017); S. T. Bailey et al., OPHTHALMOLOGY RETINA (2019)).

SUMMARY

Various implementations of the present disclosure relate to systems, methods, and devices for identifying CNV membranes in subjects. Further implementations also include systems, methods, and devices for identifying vessels in CNV membranes of subjects.

Some example methods include generating, by a first model based on at least one image of a retina of a subject, a membrane mask indicating a location of a CNV membrane in the retina; and generating, by a second model based on the membrane mask and the at least one image, a vasculature mask of the retina of the subject, the vasculature mask indicating CNV vascularization in the retina.

Some example systems include at least one processor; and memory storing instructions that, when executed by the at least one processor, cause the at least one processor to perform: a first model configured to generate, based on at least one image of a retina of a subject, a membrane mask indicating a first location of a CNV membrane in the retina; and a second model configured to generate, based on the membrane mask and the at least one image, a vasculature mask of indicating a second location of at least one vessel in the CNV membrane.

According to particular implementations, CNV membranes and vasculature can be identified based on OCT (e.g., OCTA-based) images of subject retinas. In some cases, various functions can be performed by deep learning networks, such as convolutional neural networks. Various neural networks described herein may be trained based on a variety of different retinal images representing a variety of different image qualities and pathologies. Accordingly, trained neural networks described herein can accurately segment CNV membranes and vasculature of various retinas based on various images.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The detailed description is described with reference to the accompanying figures. In the figures, the left-most digit(s) of a reference number identifies the figure in which the reference number first appears. The use of the same reference numbers in different figures indicates similar or identical components or features.

FIG. 5 illustrates an example of a convolutional block in a neural network.

FIGS. 6A to 6C illustrates transformations of 3×3 pixel input portions into 1×1 pixel output portions with different dilation rates.

FIG. 6B illustrates a transformation of a 3×3 pixel input portion into a 1×1 pixel output portion.

FIG. 6C illustrates a transformation of a 3×3 pixel input portion into a 1×1 pixel output portion.

DETAILED DESCRIPTION

Figure 1:
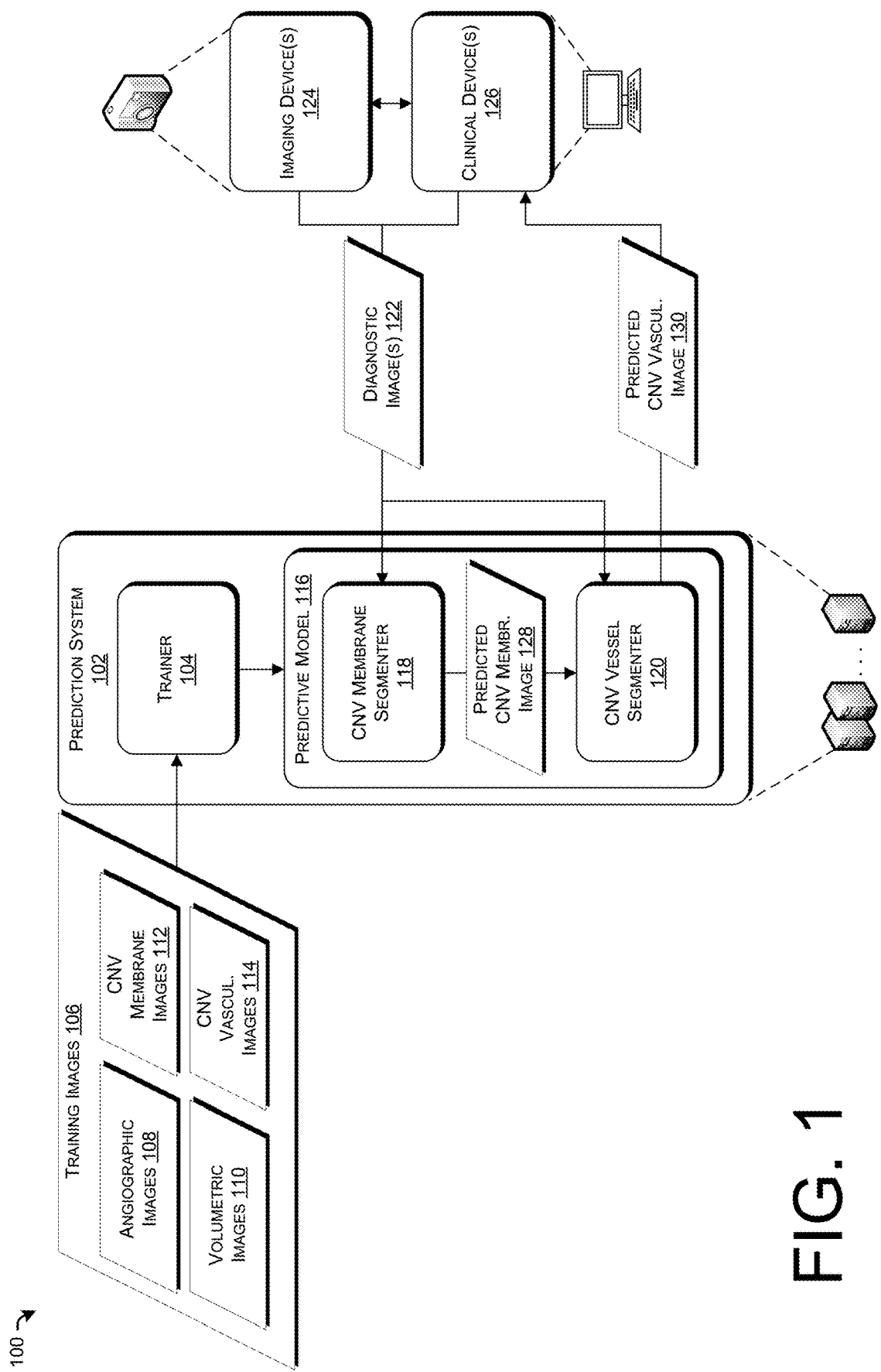
FIG. 1 illustrates an example environment for training and utilizing a predictive model to identify CNV in subjects.

This disclosure describes systems, devices, and techniques for identifying structures, such as CNV, in retinal images. Various implementations described herein can accurately identify the structures from retinal images obtained using noninvasive imaging techniques.

Despite the ubiquity of dye-based angiography in the diagnosis of CNV, dye-based angiography has a number of drawbacks. For example, dye-based angiography may be limited to two-dimensional visualization of vascular networks, rather than three-dimensional visualization. In various instances, invasive intravenous contrast dye used in dye-based angiography can cause nausea and anaphylaxis in subjects. Furthermore, dye-based angiography techniques may be associated with long acquisition times, which may prevent dye-based angiography from being used in high volume screenings or from being used to perform multiple follow-up angiograms (M. Loez-Saez et al., ANNALS OF ALLERGY, ASTHMA & IMMUNOLOGY 81, 428-430 (1998)). Accordingly, techniques that can obtain three-dimensional visualization of vascular networks of subjects using short acquisition times without administering invasive intravenous contrast dye to the subjects are needed.

Projection-resolved optical coherence angiography (PR-OCTA) provides a promising alternative to dye-based angiography. PR-OCTA scans can be obtained by processing original OCTA projection images of retinas. Unlike dye-based angiography, PR-OCTA and other OCTA-based imaging modalities are non-invasive, capable of rapid image acquisition, capable of obtaining high-resolution images, and capable of obtaining three-dimensional data sets. However, CNV identification and segmentation remains difficult even with PR-OCTA due to the susceptibility of PR-OCTA to imaging artifacts (R. F. Spade et al., RETINA 35, 2163 (2015); A. Camino et al., BIOMEDICAL OPTICS EXPRESS 8, 3053-3066 (2017); X. Wei et al., OPTICS LETTERS 43, 2204-2207 (2018)). For example, projection artifacts can cause specious flow signals in relatively anatomical layers of the retina. Projection artifacts can interfere with CNV assessment, because CNV visualization utilizes images of the outer retina, where projection artifacts are especially prominent due to proximity to the highly reflective retinal pigment epithelium (RPE).

The presence of artifacts in OCTA images can lead to careful interpretation by clinicians. Thus, evaluating OCTA images for the presence of CNV can be time consuming for clinicians. Furthermore, clinicians can evaluate CNV metrics such as vessel density or morphology by obtaining membrane and vessel segmentation but feature extraction may go awry when artifacts interfere with image analysis. Accordingly, clinicians could benefit from robust software automation solutions that are capable of accurate identification of CNV and its precise segmentation using OCTA-based images, which may include poor quality scans or highly pathological scans in which CNV is not present.

A previous attempt at automated CNV segmentation utilized a saliency-based algorithm (L. Liu et al., BIOMEDICAL OPTICS EXPRESS 6, 3564-3576 (2015)). The saliency-based algorithm uses a saliency map to highlight the dominant objects that have strong distinctiveness defined by brightness, orientation contrast, and position distance. However, this saliency-based algorithm assumes that a CNV flow signal is higher than artifacts or background noise. This assumption limits the applicability of the algorithm to real-world OCTA scans. OCTA scans can include persistent artifacts (e.g., projection artifacts and/or bulk motion artifacts) depicted in the outer retina that can cause the saliency-based algorithm to misclassify artifacts or background noise as CNV, which can lead to misdiagnosis. Furthermore, the saliency-based algorithm is unable to fully segment a large CNV membrane that fills most of its angiogram. Finally, the saliency-based algorithm always segments CNV, regardless of whether CNV actually exists in an input scan. The saliency-based approach therefore cannot accurately diagnose subjects who lack CNV.

Various implementations described herein provide accurate identification and segmentation of CNV using OCTA-based scans, which allows for the accurate diagnosis and management of neovascular AMD. In some cases, implementations described herein can provide both cross-sectional and en face visualization of CNV.

According to various examples of the present disclosure, models can perform automated retinal segmentation and CNV identification. Various implementations described herein can support a fully automated categorization and segmentation technique that can assist clinicians with diagnosing, visualizing, and monitoring CNV.

According to some examples, the models can include Convolutional Neural Networks (CNN) configured to process retinal images. In some cases, the CNNs can be trained using a training set that includes retinal images of various sample subjects, as well as previously (e.g., manually) segmented CNV areas of the sample subjects. According to some implementations, a first CNN may be trained and/or configured to identify a CNV membrane in a retinal image of a subject. A second CNN may be trained and/or configured to identify CNV vasculature in the CNV membrane based on the retinal image of the subject, as well as the CNV membrane identified by the first CNN. The CNV membrane and/or CNV vasculature can be output to a clinician via a user device. The clinician may utilize the delineated CNV membrane and vasculature to accurately diagnose and/or monitor the presence of CNV in the retina of the subject.

In various implementations, CNV areas can be accurately identified with non-dye-based imaging methods. For example, CNV areas can be accurately segmented based on PR-OCTA images. Unlike dye-based angiography, PR-OCTA is non-invasive and images are acquired easily and rapidly in the clinical setting. Various examples described herein can accurately identify and segment CNV using PR-OCTA, rather than dye-based angiography, which provides the opportunity to develop routine imaging for CNV detection and monitoring. Such monitoring allows early detection of CNV and conversion to exudative CNV, further allowing for successful intervention. Furthermore, improved quantification of CNV features can identify additional indicators for disease progression (M. Al-Sheikh et al., Retina 38, 220-230 (2018)).

According to various examples, CNV areas can be accurately identified from even low-quality OCTA scans, which may include significant projection and/or bulk-motion artifacts. Further, relatively large CNV areas (e.g., CNV areas that take up most of an OCTA image) can be accurately identified using various techniques described herein.

Example Definitions

As used herein, the term "segmentation," and its equivalents, can refer to a process of defining an image of a retina into regions. For instance, a segmentation method can be performed by defining an area of an angiogram that depicts a CNV area As used herein, the term "reflectance image" can refer to a two-dimensional B-scan of a retina, wherein the values of individual pixels of the reflectance image correspond to reflectance intensity values observed by an OCT system at respective positions corresponding to the individual pixels. One dimension of the B-scan can be defined along a depth direction. Another direction can be defined along a lateral direction of the retina (e.g., defined in a direction parallel to a direction defined between the eyes of the subject).

As used herein, the term "depth direction," and its equivalents, can refer to a direction in a reflectance image that is parallel to a direction extending between a vitreous and a Bruch's membrane of a retina depicted in the reflectance image. The depth direction may be parallel to an OCT beam incident on the retina, in some cases.

As used herein, the terms "A-line," "A-scan," and their equivalents, can refer to a one-dimensional set of pixels in a reflectance image. In particular, an A-line can extend in a direction parallel to a depth direction. A reflectance image can comprise multiple A-lines. A length of an A-line may be the same length as the reflectance image, and a width of the A-line may be a width of a single pixel length.

As used herein, the term "Optical Coherence Tomography (OCT)," and its equivalents, can refer to a noninvasive low-coherence interferometry technique that can be used to obtain depth images of tissues, such as structures within the eye. In various implementations, OCT can be used to obtain depth images of retinal structures (e.g., layers of the retina). In some cases, OCT can be used to obtain a volumetric image of a tissue. For example, by obtaining multiple depth images of retinal structures along different axes, OCT can be used to obtain a volumetric image of the retina.

As used herein, the term "Optical Coherence Tomographic Angiography (OCTA)," and its equivalents, can refer to a subset of OCT techniques that obtain images based on flow (e.g., blood flow) within an imaged tissue. Accordingly, OCTA can be used to obtain images of vasculature within tissues, such as the retina. In some cases, OCTA imaging can be performed by obtaining multiple OCT scans of the same area of tissue at different times, in order to analyze motion or flow in the tissue that occurred between the different times.

As used herein, the term "OCT image," and its equivalents, can refer to an OCT reflectance image, an OCTA image, or a combination thereof. An OCT image may be two-dimensional (e.g., one 2D projection image or one 2D depth image) or three-dimensional (e.g., a volumetric image).

As used herein, the terms "vascular," "perfusion," and the like can refer to an area of an image that depicts vasculature. In some cases, a perfusion area can refer to an area that depicts a blood vessel or another type of vasculature.

As used herein, the terms "avascular," "nonperfusion," and the like can refer to an area of an image that does not depict vasculature. In some cases, a nonperfusion area can refer to an area between blood vessels or other types of vasculature.

As used herein, the terms "blocks," "layers," and the like can refer to devices, systems, and/or software instances (e.g., Application Programming Interfaces (APIs), Virtual Machine (VM) instances, or the like) that generates an output by apply an operation to an input. A "convolutional block," for example, can refer to a block that applies a convolution operation to an input (e.g., an image). When a first block is in series with a second block, the first block may accept an input, generate an output by applying an operation to the input, and provide the output to the second block, wherein the second block accepts the output of the first block as its own input. When a first block is in parallel with a second block, the first block and the second block may each accept the same input, and may generate respective outputs that can be provided to a third block. In some examples, a block may be composed of multiple blocks that are connected to each other in series and/or in parallel. In various implementations, one block may include multiple layers.

In some cases, a block can be composed of multiple neurons. As used herein, the term "neuron," or the like, can refer to a device, system, and/or software instance (e.g., VM instance) in a block that applies a kernel to a portion of an input to the block.

As used herein, the term "kernel," and its equivalents, can refer to a function, such as applying a filter, performed by a neuron on a portion of an input to a block.

As used herein, the term "pixel," and its equivalents, can refer to a value that corresponds to an area or volume of an image. In a grayscale image, the value can correspond to a grayscale value of an area of the grayscale image. In a color image, the value can correspond to a color value of an area of the color image. In a binary image, the value can correspond to one of two levels (e.g., a 1 or a 0). The area or volume of the pixel may be significantly smaller than the area or volume of the image containing the pixel. In examples of a line defined in an image, a point on the line can be represented by one or more pixels. A "voxel" is an example of a pixel spatially defined in three dimensions.

Particular Implementations

Some particular implementations of the present disclosure will now be described with reference to FIGS. 1 to 9. However, the implementations described with reference to FIGS. 1 to 9 are not exhaustive.

FIG. 1 illustrates an example environment 100 for training and utilizing a predictive model to identify CNV in subjects. As shown in FIG. 1, the environment 100 includes a prediction system 102, which may be configured to identify CNV in subjects. In various implementations, the prediction system 102 may be embodied in one or more computing devices (e.g., servers). The prediction system 102 may include hardware, software, or a combination thereof.

The prediction system 102 may include a trainer 104, which may receive training images 106. The trainer 104 may use the training images 106 to train one or more models to identify CNV in subjects. In various implementations, the training images 106 can include previously obtained retinal images of various individuals in a sample population. These retinal images may include OCT-based images, such as OCTA scans of the retinas of the various individuals.

In various cases, the training images 106 can include angiographic images 108 of retinas of the various individuals. The angiographic images 108 may include OCTA images, such as PR-OCTA scans of the retinas of the various individuals. In some cases, the angiographic images 108 may include inner retina images, original outer retina images, slab-subtracted outer retina images, and Projection Resolved (PR) outer retina images, which may be derived from OCTA scans of the retinas of the various individuals. In some cases, the angiographic images 108 may include whole retina images (e.g., inner retinal structure volumes, outer retinal structure volumes, combinations of inner and outer retinal structure volumes) or whole OCT volumes (e.g., volumes depicting both retinal and choroidal structures). While more complex images may enhance training, limiting at least some of the angiographic images 108 to images that depict outer retinal images may be used to conserve computing and memory resources. The inner retina images may include two-dimensional projection images of the inner retinas of the various individuals. The original outer retina images may include two-dimensional projection images of the outer retinas of the various individuals. In some examples, the "inner retina" is defined as the portions of the retina defined between the Inner Limiting Membrane (ILM) and the Outer Plexiform Layer (OPL), and the "outer retina" is defined as the portions of the retina defined between the OPL and the Bruch's Membrane (BM). The slab-subtracted images may include two-dimensional images obtained by subtracting the original outer retina images from their respective inner retina images, such that the slab-subtracted images may omit at least some projection artifacts caused by inner retinal structures. Example slab subtraction techniques are described, for example, in at least L. Liu et al., Biomedical Optics Express 6, 3564-3576 (2015); Y. Jia et al., Ophthalmology 121. 1435-1444 (2014); Y. Jia et al., PNAS 201500185 (2015). The PR outer retina images can be obtained by performing projection resolved processing on the original outer retina images, such as the processing described in at least J. Wang, et al., BIOMED. OPT. EXPRESS 8(3), 1536-48 (2017) and R. C. Patel, et al., OPHTHALMOL. RETIN. 2(8), 816-26 (2018).

According to various implementations, a set of the angiographic images 108 depicting the same retina of the same individual at the same time may include multiple two-dimensional angiographic images with the same pixel dimensions. For example, each one of the angiographic images 108 may have the same pixel height and the same pixel width. In some cases, a set of the angiographic images 108 depicting the same retina may be combined into a multi-channel image, wherein each image among the set may define a channel in the multi-channel image. For instance, if the set of angiographic images 108 includes four distinct two-dimensional images, the multi-channel image may have a height defined as the pixel height of the two-dimensional images, the multi-channel image may have a width defined as the pixel width of the two-dimensional images, and the multi-channel image may have a depth of four pixels, each depth level including an individual image among the two-dimensional images.

In some implementations, the training images 106 can include volumetric images 110 of the retinas of the various individuals. The volumetric images 110 may depict various layers of the retinas of the various individuals. In some cases, the volumetric images 110 may be obtained by obtaining multiple OCT (e.g., OCTA) depth scans of each of the retinas at various axes. In some examples, the volumetric images 110 can depict various layer boundaries of the retinas, which can be obtained using a graph search technique, on the OCT depth scans. Examples of the graph search technique are provided in at least Zhang, M., et al., BIOMEDICAL OPTICS EXPRESS, 6(12), 4661-75 (2015); Guo, Y., et al., BIOMEDICAL OPTICS EXPRESS, 9(9), 4429-42 (2018); and Zang, P., et al., BIOMEDICAL OPTICS EXPRESS, 10(8), 4340-52 (2019).

According to some examples, the training images 106 can include CNV membrane images 112 of the retinas of the various individuals. The training images 106 may include CNV vasculature 114 images of the various individuals. The CNV membrane images 112 and the CNV vasculature images 114 may be manually segmented by experts. For example, one or more expert graders (e.g., at least one expert ophthalmologist) may manually identify the positions of any CNV membranes depicted in the angiographic images 108 (e.g., in the original outer retina images) using a user interface associated with an API, which may convert the identified positions of the CNV membranes to binary images indicating the positions of the CNV membranes in the angiographic images 108. Similarly, the expert grader(s) may manually identify the positions of any vasculature in the CNV membranes depicted in the angiographic images 108 using a user interface connected to an API, which may convert the identified positions of the vasculature to binary images indicating the positions of the vasculature in the CNV membranes of the angiographic images 108. In some cases, the CNV vasculature images 114 may be initially generated in accordance with the Otsu algorithm, and the expert grader(s) may confirm the position of any vasculature indicated by the Otsu algorithm. The Otsu algorithm is described in, e.g., Otsu, N., IEEE TRANSACTIONS ON SYSTEMS, MAN, AND CYBERNETICS, 9(1), 62-66 (1979). As used herein, the term "CNV membrane image" can be referred to as a "membrane mask," and the term "CNV vasculature image" may be referred to as a "vasculature mask."

In various examples, the trainer 104 is configured to use the training images 106 to train a predictive model 116, which includes a CNV membrane segmenter 118 and a CNV vasculature segmenter 120. In some cases, the predictive model 116 is a deep learning model, such as a Convolutional Neural Network (CNN) model. For instance, the CNV membrane segmenter 118 may include a first CNN and/or the CNV vasculature segmenter 120 may include a second CNN.

The term Neural Network (NN), and its equivalents, may refer to a model with multiple hidden layers, wherein the model receives an input (e.g., a vector) and transforms the input by performing operations via the hidden layers. An individual hidden layer may include multiple "neurons," each of which may be disconnected from other neurons in the layer. An individual neuron within a particular layer may be connected to multiple (e.g., all) of the neurons in the previous layer. A NN may further include at least one fully-connected layer that receives a feature map output by the hidden layers and transforms the feature map into the output of the NN.

As used herein, the term "CNN," and its equivalents, may refer to a type of NN model that performs at least one convolution (or cross correlation) operation on an input image and may generate an output image based on the convolved (or cross-correlated) input image. A CNN may include multiple layers that transforms an input image (e.g., a 3D volume) into an output image via a convolutional or cross-correlative model defined according to one or more parameters. The parameters of a given layer may correspond to one or more filters, which may be digital image filters that can be represented as images. A filter in a layer may correspond to a neuron in the layer. A layer in the CNN may convolve or cross correlate its corresponding filter(s) with the input image in order to generate the output image. In various examples, a neuron in a layer of the CNN may be connected to a subset of neurons in a previous layer of the CNN, such that the neuron may receive an input from the subset of neurons in the previous layer, and may output at least a portion of an output image by performing an operation (e.g., a dot product, convolution, cross-correlation, or the like) on the input from the subset of neurons in the previous layer. The subset of neurons in the previous layer may be defined according to a "receptive field" of the neuron, which may also correspond to the filter size of the neuron. U-Net (see, e.g., Ronneberger, et al., arXiv: 1505.04597v1, 2015) is an example of a CNN model.

The training images 106 may include a set of input images with known output images that are to be generated by the CNV membrane segmenter 118 and the CNV vasculature segmenter 120. The trainer 104 can perform various techniques to train (e.g., optimize parameters of) the CNV membrane segmenter 118 and the CNV vasculature segmenter 120 using the training images 106. For example, the trainer 104 can perform a training technique utilizing stochastic gradient descent with backpropagation, or any other machine learning training technique known to those of skill in the art.

The trainer 104 may determine optimized parameters of the predictive model 116, for example, by optimizing a loss function. In some cases, the loss may be the cross-entropy with L2 regularization. In some implementations, a cross-entropy technique can be used to test the loss. For example, the trainer 104 may apply the following Equations (1)-(3), in order to determine the parameters:

$$E = -\sum_{i=1}^{N} y_i \cdot \log(\hat{y}_i) \quad (1)$$

$$R = \alpha \sum w^T w \quad (0 \leq \alpha \leq 1) \quad (2)$$

$$T = E + R \quad (3)$$

wherein E is the cross-entropy, N is the number of classes, $y_i$ is the label, $\hat{y}_i$ is the predicted value, w is weight factor of the model, R is L2 regularization loss and T is the loss.

According to various implementations, the training images 106 may depict a variety of different retinas. For example, the training images 106 may depict retinas with CNV and without CNV. In some implementations, the training images 106 may include images captured with different levels of image quality. For instance, at least some of the training images 106 may include artifacts, such as projection artifact(s) and/or bulk-motion artifact(s). The training images 106 may include retinas obtained from individuals with a variety of different demographics (e.g., genders, ages, or the like). Further, the training images 106 may depict retinas with various pathologies. For instance, the training images 106 can depict at least one retina without CNV, at least one retina with CNV, at least one retina with Diabetic Retinopathy (DR), at least one retina with Macular Degeneration (MD) (e.g., wet and/or dry MD, Age-related MD (AMD), or the like). The variety of different retinas depicted in the training images 106 can improve the performance of the trained predictive model 116. For example, various image qualities depicted by the training images 106 may enable the predictive model 116 to accurately identify CNV in low- and high-quality images. The various pathologies depicted by the training images 106 may enable the predictive model 116 to accurately identify CNV in retinas with or without other types of pathologies.

The trainer 104 may be configured to train the predictive model 116 by optimizing various parameters within the predictive model 116 based on the training images 106. For example, the trainer 104 may input the angiographic images 108 and the volumetric images 110 into the CNV membrane segmenter 118 and compare outputs of the CNV membrane segmenter 118 to the CNV membrane images 112. The trainer 104 may further modify various parameters of the CNV membrane segmenter 118 (e.g., filters in the first CNN) in order to ensure that the outputs of the CNV membrane segmenter 118 are sufficiently similar and/or identical to the CNV membrane images 112. In some cases, the trainer 104 may input the angiographic images 108, the volumetric images 110, and the CNV membrane images 112 into the CNV vasculature segmenter 120 and compare outputs of the CNV vasculature segmenter 120 to the CNV vasculature images 114. The trainer 104 may further modify various parameters of the CNV vasculature segmenter 120 (e.g., filters in the second CNN) in order to ensure that the outputs of the CNV vasculature segmenter 120 are sufficiently similar and/or identical to the CNV vasculature images 114. In some cases, the trainer 104 may further feed (CNV membrane) images generated by the CNV membrane segmenter 118 into the CNV vasculature segmenter 120, and optimize the parameters of the CNV vasculature segmenter 120 based on the images generated by the CNV membrane segmenter 118.

The trainer 104 may be configured to train the CNV membrane segmenter 118 to identify the presence of a CNV membrane in one or more diagnostic images 122. The diagnostic image(s) 122, for example, may include angiographic and/or volumetric images of a retina of a single subject. In some cases, the trainer may be configured to train the CNV membrane segmenter 118 to identify whether CNV is present in the retina depicted by the diagnostic image(s) 122. For instance, the CNV membrane segmenter 118 may be trained to identify that the retina includes at least one CNV membrane.

The trainer 104 may be configured to train the CNV vasculature segmenter 120 to identify vasculature in the at least one CNV membrane depicted in the diagnostic image(s) 122. For instance, the CNV vasculature segmenter 120 can be trained to identify positions of blood vessels in a CNV membrane depicted in the diagnostic image(s) 122.

The diagnostic image(s) 122 may be obtained by at least one imaging device 124 and/or at least one clinical device 126. The imaging device(s) 124 may include, for example, a OCTA (e.g., a PR-OCTA) imaging device. In some cases, the imaging device(s) 124 may include at least one camera, which may generate digital images (e.g., three-dimensional volumetric images) of the retina of a subject based on the OCTA (e.g., PR-OCTA) scan. In some cases, the imaging device 124 further obtains at least some of the training images 106. Accordingly, in some implementations, the training images 106 and the diagnostic image(s) 122 may be generated using the same imaging system.

In a particular example, the imaging device(s) 124 obtains the diagnostic image(s) 122 by performing a PR-OCTA scan on a subject. The diagnostic image(s) 122 may include a PR-OCTA scan of a retina of the subject. In some cases, the imaging device(s) 124 may further process the PR-OCTA scan of the subject. For instance, the imaging device(s) 124 may obtain a volumetric scan of the retina of the subject using the PR-OCTA scan. In some cases, the imaging device(s) 124 may obtain an inner retina image of the subject using the PR-OCTA scan. According to some examples, the imaging device(s) 124 can obtain at least one outer retina image of the subject using the PR-OCTA scan. The outer retina image(s) may include an original outer retina image, a slab-subtracted outer retina image, and/or a PR outer retina image of the retina of the subject. The diagnostic image(s) 122 may include the inner retina image and/or the outer retina image(s). In some cases, the diagnostic image(s) 122 may include more complex images, such as whole retina images (e.g., inner retinal structure volumes, outer retinal structure volumes, combinations of inner and outer retinal structure volumes) or whole OCT volumes (e.g., volumes depicting both retinal and choroidal structures). Although these more complex images may enhance the accuracy of various implementations, they may also increase the use of computing and/or memory resources utilized to perform various analyses described herein.

The imaging device(s) 124 can provide the diagnostic image(s) 122 to the CNV membrane segmenter 118. The CNV membrane segmenter 118 may have been previously trained by the trainer 104. In various examples, the CNV membrane segmenter 118 may be configured to generate a predicted CNV membrane image 128 based on the diagnostic image(s) 122. The predicted CNV membrane image 128 may depict a CNV membrane in the retina of the subject. In some cases, the CNV membrane segmenter 118 may combine and perform one or more convolutions and/or cross-correlations on the diagnostic image(s) 122 with one or more filters to generate the CNV membrane image 128. In some cases, the CNV membrane image 128 may be a two-dimensional binary image with the same pixel height and width as the diagnostic image(s) 122. A first set of pixels in the CNV membrane image 128 may correspond to a first set of pixels in the diagnostic image(s) 122 that depict the CNV membrane in the retina of the subject. For instance, the xy dimensions of the first set of the pixels in the CNV membrane image 128 may be the same as the xy dimensions of the first set of pixels in the diagnostic image(s) 122. A second set of pixels in the CNV membrane image 128 may correspond to a second set of pixels in the diagnostic image(s) 122 that depict a non-CNV area in the retina of the subject. For instance, the xy dimensions of the second set of the pixels in the CNV membrane image 128 may be the same as the xy dimensions of the second set of pixels in the diagnostic image(s) 122. In some cases, in which the retina of the subject is without a CNV membrane, the pixels of the CNV membrane image 128 may have the same value.

According to some implementations, the CNV membrane segmenter 118 may include a size cutoff filter, which may remove any predicted CNV membrane areas from the CNV membrane image 128 that are smaller than a threshold size (e.g., a threshold width, threshold depth, and/or threshold height). The size cutoff filter may prevent the CNV membrane segmenter 118 from identifying artifacts as CNV membrane areas within the CNV membrane image 128.

The imaging device(s) 124 may further provide the diagnostic image(s) 122 to the CNV vasculature segmenter 120. In various implementations, the CNV membrane segmenter 118 may further input the CNV membrane image 128 into the CNV vasculature segmenter 120. The CNV vasculature segmenter 120 may be configured to identify the position of at least on vessel in the CNV membrane depicted in the diagnostic image(s) 122 using the diagnostic image(s) 122 and/or the CNV membrane image 128. According to various examples, the CNV vasculature segmenter 120 may combine and perform one or more convolutions and/or cross-correlations on the diagnostic image(s) 122 and/or the CNV membrane image 128 with one or more filters to generate a predicted CNV vasculature image 130. The CNV vasculature image 130 may be a binary image with the same dimensions as the diagnostic image(s) 122. A first set of pixels in the CNV vasculature image 130 may correspond to a third set of pixels in the diagnostic image(s) 122 that depict vessels in the CNV membrane of the subject's retina. For example, the xy dimensions of the first set of pixels in the CNV vasculature image 130 may be the same as the xy dimensions of the third set of pixels in the diagnostic image(s) 122. A second set of pixels in the CNV vasculature image 130 may correspond to a fourth set of pixels in the diagnostic image(s) 122 that depict at least one avascular area in the retina of the subject and/or an area outside of the CNV membrane in the retina of the subject.

The CNV vessel segmenter 120 may output the CNV vascular image 130 to the clinical device(s) 126. In various implementations, the clinical device(s) 126 may output the vascular image 130 to a user (e.g., a clinician) via a user interface. For example, the clinical device(s) 126 may output the CNV vascular image 130 on a display of the clinical device(s) 126. In some cases, the predicted CNV membrane image 128 is also provided to the clinical device(s) 126 and/or output to the user via the user interface. In some cases, the clinical device(s) 126 may output an overlay image that depicts at least one of the diagnostic image(s) 122 overlaid with the CNV membrane image 128 and/or the CNV vascular image 130. Accordingly, various implementations of the present disclosure can assist clinicians and other users with identifying and monitoring CNV in the subject, as well as other subjects under observation.

In some implementations, the prediction system 102 may be hosted on one or more devices (e.g., servers) that are located remotely from the clinical device(s) 112. For example, the prediction system 102 may receive and evaluate diagnostic OCT images 114 from multiple clinical devices 112 located in various locations (e.g., various healthcare facilities).

According to certain implementations, the prediction system 102 and/or the clinical device(s) 126 may interface with an Electronic Medical Record (EMR) system (not illustrated). The diagnostic image(s) 122, the predicted CNV membrane image 128, the predicted CNV vascular image 130, information about the diagnostic image(s) 122, information about the predicted CNV membrane image 128, information about the predicted CNV vascular image 130, and the like, may be stored and/or accessed in memory stored at the EMR system.

In various implementations, at least one of the prediction system 102, the trainer 104, the neural network predictive model 116, the imaging device(s) 124, or the clinical device(s) 126 may include at least one system (e.g., a distributed server system), at least one computing device, at least one software instance (e.g., a Virtual Machine (VM)) hosted on system(s) and/or device(s), or the like. For instance, instructions to execute functions associated with at least one of the prediction system 102, the trainer 104, the neural network predictive model 116, the imaging device(s) 124, or the clinical device(s) 126 may be stored in memory. The instructions may be executed, in some cases, by at least one processor.

According to various examples, at least one of the training images 106, the diagnostic image(s) 122, the predicted CNV membrane image 128, or the predicted CNV vascular image 130 may include data packaged into at least one data packet. In some examples, the data packet(s) can be transmitted over wired and/or wireless interfaces. According to some examples, the data packet(s) can be encoded with one or more keys stored by at least one of the prediction system 102, the trainer 104, the neural network predictive model 116, the imaging device(s) 124, or the clinical device(s) 126, which can protect the data paged into the data packet(s) from being intercepted and interpreted by unauthorized parties. For instance, the data packet(s) can be encoded to comply with Health Insurance Portability and Accountability Act (HIPAA) privacy requirements. In some cases, the data packet(s) can be encoded with error-correcting codes to prevent data loss during transmission.

Figure 2:
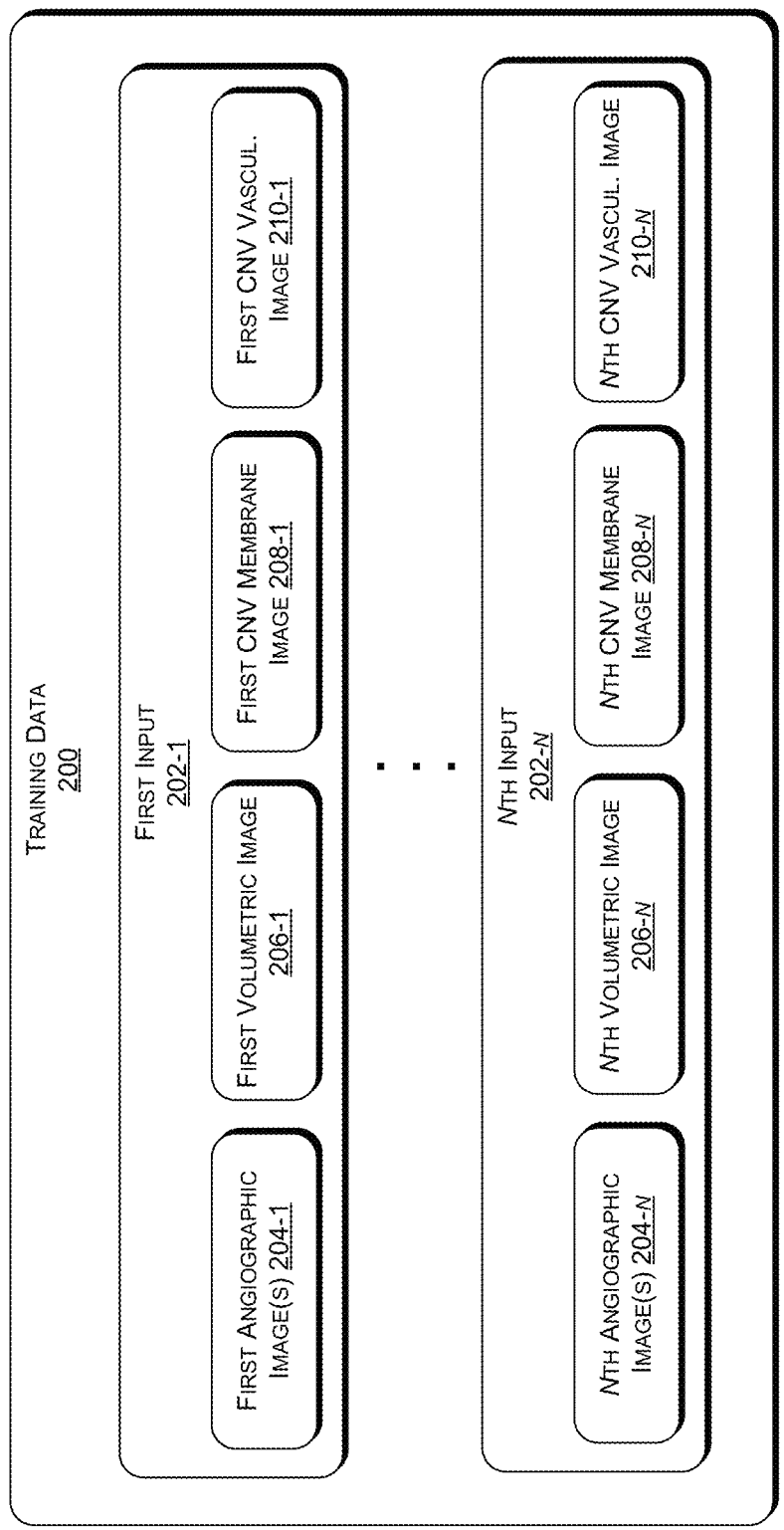
FIG. 2 illustrates an example of training data, which may be used to train a predictive model according to various implementations of the present disclosure.

FIG. 2 illustrates an example of training data 200, which may be used to train a predictive model according to various implementations of the present disclosure. In some cases, the training data 200 can be the training images 106 described above with reference to FIG. 1.

The training data 200 may include n inputs 202-1 to 202-n, wherein n is a positive integer. Each one of the inputs 202-1 to 202-n may correspond to a retina of a single individual obtained at a particular time. For example, a first input 202-1 may include images of a first retina of a first example individual that was scanned on a first date, and a second input 202-2 may include images of a second retina of a second example individual that was scanned on a second date. In some cases, the first individual and the second individual can be the same person, but the first date and the second date may be different days. In some implementations, the first individual and the second individual can be different people, but the first date and the second date can be the same days.

Each one of the inputs 202-1 to 202-n may include multiple images of the retina of a corresponding individual. For example, the first input 202-1 may include at least one first angiographic image 204-1, a first volumetric image 206-1, a first CNV membrane image 208-1, and a first CNV vasculature image 210-1, all of which depict the retina of the first individual. Descriptions of example angiographic images, volumetric images, CNV membrane images, and CNV vasculature images are described above with reference to FIG. 1.

According to various implementations, the training data 200 is used to train a predictive model. In some examples, the predictive model includes at least one CNN including various parameters that are optimized based on the training data 200. For instance, a first CNN in the predictive model may be optimized to transform the angiographic image(s) 204-1 to 204-n and the volumetric images 206-1 to 206-n respectively into the CNV membrane images 208-1 to 208-n. In some cases, a second CNN in the predictive model can be optimized to transform the angiographic image(s) 204-1 to 204-n, the volumetric images 206-1 to 206-n, and the CNV membrane images 208-1 to 208-n respectively into the CNV vasculature images 210-1 to 210-n.

Figure 3:
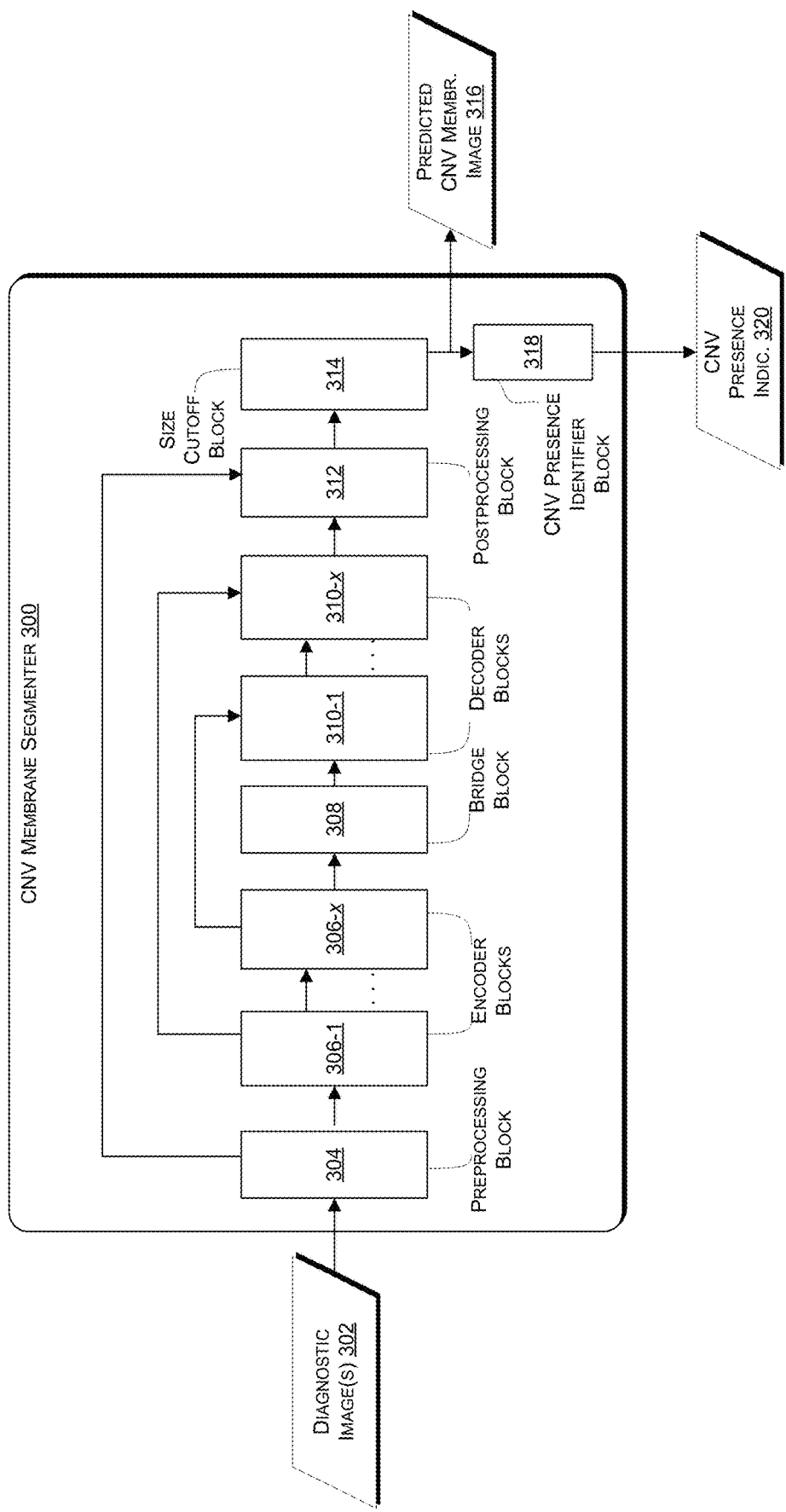
FIG. 3 illustrates an example of a CNV membrane segmenter.

FIG. 3 illustrates an example of a CNV membrane segmenter 300, such as the CNV membrane segmenter 118 described above with reference to FIG. 1. As illustrated, the CNV membrane segmenter 300 includes multiple blocks that identify the presence of a CNV membrane in a retina by performing various transformations on inputs. The CNV membrane segmenter 300 includes a CNN, for example.

The CNV membrane segmenter 300 receives diagnostic images 302. In various examples, the diagnostic images 302 include at least one image of a retina of a subject. For instance, the diagnostic images 302 include and/or are based on an OCTA image (e.g., a PR-OCTA image) of the retina of the subject. In some cases, the diagnostic image(s) 302 include at least one two-dimensional image of the retina, such as at least one of an inner retina projection image, an original outer retina image, a slab-subtracted outer retina image, or a PR outer retina image. According to some implementations, the diagnostic images 302 include a volumetric image depicting the retina of the subject. The volumetric image may be based on a volumetric OCT image of the retina of the subject.

A preprocessing block 304 performs various operations on the diagnostic images 302. In some examples, the preprocessing block 304 includes at least one concatenation layer that combines the diagnostic images 302 into a single input image. For example, each 2D pixel depth image of the diagnostic images 302 can be input into the preprocessing block 304 as a separate channel. A concatenation layer may concatenate multiple inputs in a depth axis. In some examples, the preprocessing block 304 includes at least one convolution layer, at least one batch normalization layer, and at least one Rectified Linear Unit (ReLU) layer. A convolution layer may be configured to convolve and/or cross-correlate an input image with a digital filter. A batch normalization layer may be configured to normalize input images by fixing activations to be zero-mean and with a unit standard deviation. A batch normalization block may reduce overfitting, which can make the model more stable during training. A ReLU layer may be configured to remove negative values (e.g., pixels) from an input image by setting the negative values to 0. In some cases, the preprocessing block 304 may include a maximum pooling layer. The max pooling layer, if present, is configured to generate an output image including maximums of sections (e.g., 2×2 pixel sections) of an input image. In some cases, the output image of a max pooling layer may have smaller dimensions than the input image to the max pooling layer. In some examples, a max pooling layer may reduce (e.g., halve) the spatial size of an input to reduce the amount of parameters and computation in the overall neural network.

Encoder blocks 306-1 to 306-x (where x is a positive integer) process an output of the preprocessing block 304. In various implementations, the encoder blocks 306-1 to 306-x are arranged in series, such that at least one encoder block receives an input from a previous encoder block in the series and may provide an output to a next encoder block in the series, and so on. Any one of the encoder blocks 306-1 to 306-x may include at least one of a convolution layer, a batch normalization layer, or a ReLU layer.

According to various implementations, the encoder blocks 306-1 to 306-x may include atrous convolution layers. An atrous convolution layer convolves an input using a sparse kernel. The input to a neuron in an atrous convolution layer may include a subset of pixels in an image input into the atrous convolution layer, wherein the subset of pixels are separated in the image by gaps of pixels that are ignored by the neuron. In various cases, the length of the gaps are known has the "rate" (also referred to as "dilation rate") of the kernel. In some implementations, the rates of atrous convolution layers in the encoder blocks 306-1 to 306-x increase along the series of the encoder blocks 306-1 to 306-x. For instance, a first atrous convolution layer in the first encoder block 306-1 may have a first rate, a second atrous convolution layer in a second encoder block among the encoder blocks 305-1 to 306-x may have a second rate, and an xth atrous convolution layer in the xth encoder block 306-x may have an $2^{(x-1)}$th rate, wherein the second rate is greater than the first rate and the xth rate is greater than the second rate. In some cases, the rates of the atrous convolution layers in the encoder blocks 306-1 to 306-x can range from 1 to $2^{(x-1)}$.

In various implementations, a single encoder block among the encoder blocks 306-1 to 306-x may include multiple sets of convolution-batch normalization-ReLU layers arranged in series. That is, the single encoder block may include a convolution layer, a batch normalization layer, and a first ReLU layer arranged in series, and possibly another convolution layer, batch normalization layer, and ReLU layer arranged in series after the first ReLU layer. The convolution layers within a single encoder block may apply the same dilation rate, in various cases. According to some implementations, concatenation layers may be arranged between the sets of convolution-batch normalization-ReLU sets in the series, which may concatenate outputs of previous convolution-batch normalization-ReLU sets in the series. An example concatenation layer may perform, for instance 1×1 convolutions on two or more inputs to the example concatenation layer. For instance, an input to an example encoder block may be processed by first convolution-batch normalization-ReLU set, which may provide its output to a concatenation layer that concatenates the input to the example encoder block with the output of the first convolution-batch normalization-ReLU set, wherein the output of the concatenation layer is provided to a second convolution-batch normalization-ReLU set in the example encoder block. The final concatenation layer in the example encoder block may concatenate the input to the example encoder block with each output of each previous convolution-batch normalization-ReLU set in the series, before providing its output to the final convolution-batch normalization-ReLU set in the series.

The xth encoder block 306-x may be configured to provide its output to a bridge block 308. The bridge block 308, in some cases, may have the same or similar structure to at least one of the encoder blocks 306-1 to 306-x. For instance, the bridge block 308 may be referred to as an encoder block, in some cases. The bridge block 308 may include at least one of a convolution layer, a batch normalization layer, or a ReLU layer. According to some examples, the bridge block 308 may include multiple sets of convolution-batch normalization-ReLU layers arranged in series and multiple concatenation layers arranged between the sets of convolution-batch normalization-ReLU layers, similar to implementations of the encoder blocks 306-1 to 306-x described above. In some cases, the bridge block 308 includes at least one atrous convolutional layer. The rate of the atrous convolutional layer(s) in the bridge block 308 may be greater than the rate of the atrous convolutional layer(s) in the xth encoder block 306-x.

Further, at least some of the encoder blocks 306-1 to 306-x may be configured to provide their respective output images to corresponding decoder blocks among decoder blocks 310-1 to 310-x. For example, a first encoder block 306-1 may provide its output to the second encoder block 306-2 as well as to the xth decoder block 310-x. The first decoder block 310-1 may receive the output from the xth encoder block 306-1 as well as an output from the bridge block 308. The second decoder block may receive the output from the x−1th encoder block as well as the output from the first decoder block 310-1, and so on. In various implementations, the decoder block(s) 310-1 to 310-x are arranged in series, such that at least one decoder block receives an input from a previous block (e.g., a previous encoder block or a previous decoder block) in the series and may provide an output to a next decoder block in the series, and the like. In various implementations, any one of the decoder blocks 310-1 to 310-x may include a concatenation layer configured to concatenate multiple input images. For instance, the first decoder block 310-1 may include a concatenation layer configured to concatenate the output from the first encoder block 306-1 with the output from the xth encoder block 306-x, which are both input into the first decoder block 310-1. Any one of the decoder blocks 310-1 to 310-x may include at least one of a convolution layer, a batch normalization layer, or a ReLU layer. For example, an example one of the decoder blocks 310-1 to 310-x may include a set of convolution-batch normalization-ReLU layers arranged in series.

According to various implementations, the decoder blocks 310-1 to 310-x may include several convolution layers. In some cases, the convolution layers in the decoder blocks 310-1 to 310-x may utilize general kernels (e.g., 3×3 kernels) without dilation to interpret the features for CNV membrane segmentation.

A postprocessing block 312 may receive an input from the decoder blocks 310-1 to 310-x and perform one or more operations on the input to generate an output of the postprocessing block 312. In various implementations, the postprocessing block 312 may receive the output of the preprocessing block 304 and the output from the xth decoder block 310-x as inputs. The postprocessing block 312, in some cases, may include an upsampling layer (e.g., a x2 upsampling layer) that performs an upsampling operation on the output of the xth decoder block 310-x. For instance, the upsampling layer may double the output of the xth decoder block 310-x. In some cases, the postprocessing block 312 may include a concatenation layer that concatenates an output from the preprocessing block 304 (e.g., the input to the max pooling layer in the preprocessing block 304) with the output of the upsampling layer.

In some implementations, the postprocessing block 312 may include one or more parallelized multi-scale feature extraction layers. In various implementations, the parallelized multi-scale feature extraction layer can include multiple sets of convolution-batch normalization-ReLU layers arranged in parallel, as well as a concatenation layer that concatenates the outputs of the sets of convolution-batch normalization-ReLU layers. In some cases, the convolution layers in the respective sets of convolution-Batch normalization-ReLU layers may have different dilation rates. For instance, an input to the parallelized multi-scale feature extraction layer may be fed, independently, into each one of the sets of convolution-batch normalization-ReLU layers, wherein the different convolution layers in the respective sets apply different dilation rates (e.g., ranging from 1 to 32). The outputs of the sets of convolution-batch normalization-ReLU layers may be fed into a concatenation layer, which may concatenate the outputs into a single image. In some cases, the single image output by the parallelized multi-scale feature extraction layer may be fed into convolution-batch normalization-softmax activation layers for decision-making to generate probability maps of CNV membrane and background.

According to some examples, the postprocessing block 312 includes a softmax layer that performs an intermediary probability map generation from image(s) output by parallelized multi-scare feature extraction layer (or an intermediary convolution layer present between the parallelized multi-scale feature extraction layer and the softmax layer). The input to the softmax activation layer can be the output from previous parallelized multi-scale feature extraction layer block (or the output from the convolution layer present between the parallelized multi-scale feature extraction layer and the softmax layer). The output of the softmax activation function may be a probability map, wherein each pixel in the probability map corresponds to a probability that the corresponding pixel in the diagnostic images 302 depicts a portion of a CNV membrane. For instance, each pixel in the probability map may have a value in a range from 0 to 1. The final output by the final decision layer may be a binary image corresponding to an initial estimate of at least one CNV membrane area in the diagnostic image(s) 302. In some cases, the final decision layer may convert each pixel of the probability map whose value is at least a particular threshold (e.g., 0.5) to a first binary value (e.g., 1), and may convert each pixel of the probability map whose value is below the particular threshold to a second binary value (e.g., 0). As an alternative to the softmax layer, in some cases, the postprocessing block 312 includes a sigmoid activation layer that performs a sigmoid activation function.

In various implementations, the output of the postprocessing block 312 is input into a size cutoff block 314. The size cutoff block 314 may be configured to filter out one or more areas of estimated CNV membrane in the output of the postprocessing block 312 that are smaller than a cutoff size (e.g., defined according to a height and/or width threshold, such as a square, rectangle, or any other two-dimensional shape with an area of 0.004 mm$^2$). Accordingly, the size cutoff block 314 may prevent artifacts in the original diagnostic image(s) 302 from being identified as CNV membranes. The output of the size cutoff block 314 may be a predicted CNV membrane image 316. According to various implementations, the predicted CNV membrane image 316 may be a binary image identifying a position of at least one CNV membrane depicted in the diagnostic image(s) 302.

In some cases, the predicted CNV membrane image 316 is also input into a CNV presence identifier block 318. The CNV presence identifier block 318 may be configured to identify whether any CNV membrane is predicted as being present, using the predicted CNV membrane image 316. For instance, if any size of CNV membrane area is indicated as being present in the predicted CNV membrane image 316, the CNV presence identifier block 318 may output a CNV presence indicator 320 that indicates that the retina depicted in the diagnostic image(s) 302 has CNV. If there are no CNV membrane areas indicated as being present in the predicted CNV membrane image 316, the CNV presence indicator 320 may indicate that the diagnostic image(s) 302 do not depict a retina with CNV. In some cases, the CNV presence indicator 320 has a binary data format (e.g., "1" or "true" indicating presence of CNV, and "0" or "false" indicating absence of CNV).

Figure 4:
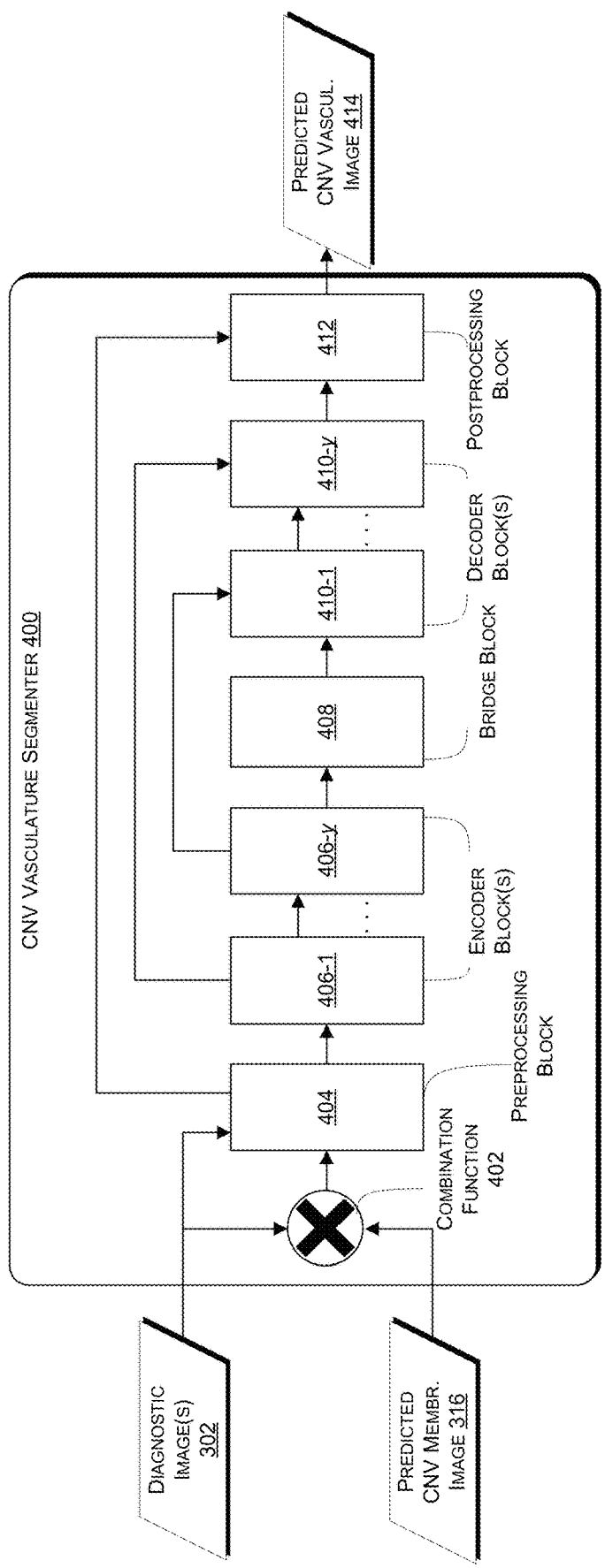
FIG. 4 illustrates an example of a CNV vasculature segmenter.

FIG. 4 illustrates an example of a CNV vasculature segmenter 400, such as the CNV vasculature segmenter 120 described above with reference to FIG. 1. As illustrated, the CNV vasculature segmenter 400 includes multiple blocks that identify the presence of vasculature in a CNV membrane of a retina by performing various transformations on inputs. The CNV vasculature segmenter 300 includes a CNN, for example.

The CNV vasculature segmenter 400 includes a combination function 402, which may be configured to combine the diagnostic image(s) 302 with the predicted CNV membrane image 318. In some cases, the combination function 402 may be configured to pixel-by-pixel multiply at least some of the diagnostic image(s) 302 with the predicted CNV membrane image 318. For example, a first value of a first pixel in the diagnostic image(s) 302 located at (x=a,y=b) is multiplied by a second value of a second pixel in the predicted CNV membrane image 316 located at (x=a,y=b), and the product of the first and second values is a third value located at (x=a,y=b) of the output image of the combination function 402, and so on. Accordingly, the output of the combination function 402 may be an image of a portion of the diagnostic image(s) 302 that depicts the identified CNV membrane. According to some examples, the combination function 402 combines angiographic images among the diagnostic image(s) 302 with the CNV membrane image 318. The combination function 402 may output an image based on the combined diagnostic image(s) 302 and the predicted CNV membrane image 318.

The combination function 402 may provide its output image to a preprocessing block 404 in the CNV vasculature segmenter 400. The preprocessing block 404 may include, for instance, a concatenation layer that combines a volumetric image among the diagnostic image(S) 302 with the output of the combination function 402. In some cases, the preprocessing block may include at least one convolution layer, at least one batch normalization layer, and/or at least one ReLU layer. For example, the preprocessing block 404 may include at least one first set of convolution-batch normalization-ReLU layers that perform operations on the volumetric image, at least one second set of convolutional-batch normalization-ReLU layers that perform operations on the combined angiographic images and the CNV membrane image 318, wherein the first and second set of layers feed their respective outputs into the concatenation layer. In some instances, the preprocessing block 404 further includes at least one third set of convolution-batch normalization-ReLU layers that perform operations on the output of the concatenation layer.

Encoder blocks 406-1 to 406-y (where y is a positive integer) process an output of the preprocessing block 404. In various implementations, the encoder block(s) 406-1 to 406-y are arranged in series, such that at least one encoder block receives an input from a previous encoder block in the series and may provide an output to a next encoder block in the series, and so on. Any one of the encoder block(s) 406-1 to 406-y may include at least one of a convolution layer, a batch normalization layer, or a ReLU layer.

According to various implementations, the encoder blocks 406-1 to 406-y may include atrous convolution layers. In some implementations, the rates of atrous convolution layers in the encoder blocks 406-1 to 406-y increase along the series of the encoder blocks 406-1 to 406-y. For instance, a first atrous convolution layer in the first encoder block 406-1 may have a first rate, a second atrous convolution layer in a second encoder block among the encoder blocks 406-1 to 406-y may have a second rate, and a yth atrous convolution layer in the yth encoder block 406-y may have an $2^{(y-1)}$th rate, wherein the second rate is greater than the first rate and the yth rate is greater than the second rate. In some cases, the rates of the atrous convolution layers in the encoder blocks 406-1 to 406-y can range from 1 to $2^{(y-1)}$. For instance, the range of rates of the atrous convolution layers in the encoder blocks 406-1 to 406-y may be smaller than the range of rates of the atrous convolution layers in the encoder blocks 306-1 to 306-x.

In various implementations, a single encoder block among the encoder blocks 406-1 to 406-y may include multiple sets of convolution-batch normalization-ReLU layers arranged in series. The convolution layers within a single encoder block may apply the same dilation rate, in various cases. According to some implementations, concatenation layers may be arranged between the sets of convolution-batch normalization-ReLU sets in the series, which may concatenate outputs of previous convolution-batch normalization-ReLU sets in the series. An example concatenation layer may perform, for instance 1×1 convolution on two or more inputs to the example concatenation layer. For instance, an input to an example encoder block may be processed by first convolution-batch normalization-ReLU set, which may provide its output to a concatenation layer that concatenates the input to the example encoder block with the output of the first convolution-batch normalization-ReLU set, wherein the output of the concatenation layer is provided to a second convolution-batch normalization-ReLU set in the example encoder block. The final concatenation layer in the example encoder block may concatenate the input to the example encoder block with each output of each previous convolution-batch normalization-ReLU set in the series, before providing its output to the final convolution-batch normalization-ReLU set in the series.

The yth encoder block 406-y may be configured to provide its output to a bridge block 408. The bridge block 408, in some cases, may have the same or similar structure to at least one of the encoder blocks 406-1 to 406-y. For instance, the bridge block 408 may be referred to as an encoder block, in some cases. The bridge block 408 may include at least one of a convolution layer, a batch normalization layer, or a ReLU layer. According to some examples, the bridge block 408 may include multiple sets of convolution-batch normalization-ReLU layers arranged in series and multiple concatenation layers arranged between the sets of convolution-batch normalization-ReLU layers, similar to implementations of the encoder blocks 406-1 to 406-y described above. In some cases, the bridge block 408 includes at least one atrous convolutional layer. The rate of the atrous convolutional layer(s) in the bridge block 408 may be greater than the rate of the atrous convolutional layer(s) in the yth encoder block 406-y.

Further, at least some of the encoder blocks 406-1 to 406-y may be configured to provide their respective output images to corresponding decoder blocks among decoder blocks 410-1 to 410-y. For example, a first encoder block 406-1 may provide its output to a second encoder block among the encoder blocks 406-1 to 406-y as well as the yth decoder block 410-y. The first decoder block 410-1 may receive the output from the bridge block 408 as well as an output from the yth encoder block 406-y. The second decoder block 410-2 may receive the output from the y−1th encoder block 406-y−1 as well as the output from the first decoder block 410-1, and so on. In various implementations, the decoder block(s) 410-1 to 410-y are arranged in series, such that at least one decoder block receives an input from a previous block (e.g., a previous encoder block or a previous decoder block) in the series and may provide an output to a next decoder block in the series, and the like. In various implementations, any one of the decoder block(s) 410-1 to 410-y may include a concatenation layer configured to concatenate multiple input images. For instance, the first decoder block 410-1 may include a concatenation layer configured to concatenate the output from the first encoder block 406-1 with the output from the yth encoder block 406-y, which are both input into the first decoder block 410-1. Any one of the decoder blocks 410-1 to 410-y may include at least one of a convolution layer, a batch normalization layer, or a ReLU layer.

According to various implementations, the decoder blocks 410-1 to 410-y may include several convolution layers. In some cases, the convolution layers in the decoder blocks 410-1 to 410-y may utilize general kernels (e.g., 3×3 pixel kernels) without dilation to interpret the features for CNV vasculature segmentation. In some implementations, atrous kernels can be utilized in both the encoder blocks 406-1 to 406-y and the decoder blocks 410-1 to 410-y.

The CNV vasculature segmenter 400 may further include a postprocessing block 412, which may perform various operations on an output of the decoder blocks 410-1 to 410-y as well as the output of the preprocessing block 404. According to some implementations, the postprocessing block 412 may include a concatenation layer that is configured to concatenate the output of the yth decoder block 410-y with the output of the preprocessing block 404. In some examples, the postprocessing block 412 includes a parallelized multi-scale feature extraction layer that processes the output of the concatenation layer. The postprocessing block 412 may include at least one set of convolution-batch normalization-ReLU layers that process the output of the parallelized multi-scale feature extraction layer. In some cases, the postprocessing block 412 also includes a convolution-batch normalization-softmax activation layer, which may convert the output from the the parallelized multi-scale feature extraction layer to CNV vasculature image 414.

In some cases, the predicted CNV vasculature image 414 corresponds to the predicted CNV vasculature image 130 described above with reference to FIG. 1. The predicted CNV vasculature image 414 may indicate positions of blood vessels in the CNV membrane depicted in the diagnostic image(s) 302. In some cases, the CNV vasculature image 130 can be output (e.g., displayed) to a user (e.g., a clinician). For instance, the CNV vasculature image 130 may assist the user with identifying, diagnosing, and/or monitoring CNV in a patient whose retina is depicted by the diagnostic image(s) 302.

FIG. 5 illustrates an example of a convolutional block 500 in a neural network. In some examples, the block 500 can represent any of the convolutional blocks and/or layers described herein. For instance, the block 500 can represent an atrous convolutional block, in some cases.

The convolutional block 500 may include multiple neurons, such as neuron 502. In some cases, the number of neurons may correspond to the number of pixels in at least one input image 504 input into the block 500. Although one neuron is illustrated in each of FIG. 5, in various implementations, block 500 can include multiple rows and columns of neurons.

In particular examples, the number of neurons in the block 500 may be less than or equal to the number of pixels in the input image(s) 504. In some cases, the number of neurons in the block 500 may correspond to a "stride" of neurons in the block 500. In some examples in which first and second neurons are neighbors in the block 500, the stride may refer to a lateral difference in an input of the first neuron and an input of the second neuron. For example, a stride of one pixel may indicate that the lateral difference, in the input image(s) 504, of the input of the first neuron and the input of the second neuron is one pixel.

Neuron 502 may accept an input portion 506. The input portion 506 may include one or more pixels in the input image(s) 504. A size of the input portion 506 may correspond to a receptive field of the neuron 502. For example, if the receptive field of the neuron 502 is a 3×3 pixel area, the input portion 506 may include at least one pixel in a 3×3 pixel area of the input image(s) 504. The number of pixels in the receptive field that are included in the input portion 506 may depend on a dilation rate of the neuron 502.

In various implementations, the neuron 502 may convolve (or cross-correlate) the input portion 506 with a filter 508. The filter may correspond to at least one parameter 510, which may represent various optimized numbers and/or values associated with the neuron 502. In some examples, the parameter(s) 610 are set during training of a neural network including the block 600.

The result of the convolution (or cross-correlation) performed by the neuron 502 may be output as an output portion 512. In some cases, the output portion 512 of the neuron 502 is further combined with outputs of other neurons in the block 500. The combination of the outputs may, in some cases, correspond to an output of the block 500. Although FIG. 5 depicts a single neuron 502, in various examples described herein, the block 500 may include a plurality of neurons performing operations similar to the neuron 502.

FIGS. 6A to 6C illustrate examples of dilation rates. In various implementations, the dilation rates illustrated in FIGS. 6A to 6C can be utilized by a neuron, such as the neuron 502 illustrated in FIG. 5.

FIG. 6A illustrates a transformation 600 of a 3×3 pixel input portion 602 into a 1×1 pixel output portion 604. The dilation rate of the transformation 600 is equal to 1. The receptive field of a neuron utilizing the transformation 600 is a 3×3 pixel area.

FIG. 6B illustrates a transformation 606 of a 3×3 pixel input portion 608 into a 1×1 pixel output portion 610. The dilation rate of the transformation 606 is equal to 2. The receptive field of a neuron utilizing the transformation 606 is a 5×5 pixel area.

FIG. 6C illustrates a transformation 612 of a 3×3 pixel input portion 614 into a 1×1 pixel output portion 616. The dilation rate of the transformation 612 is equal to 4. The receptive field of a neuron utilizing the transformation 600 is a 9×9 pixel area.

Figure 7:
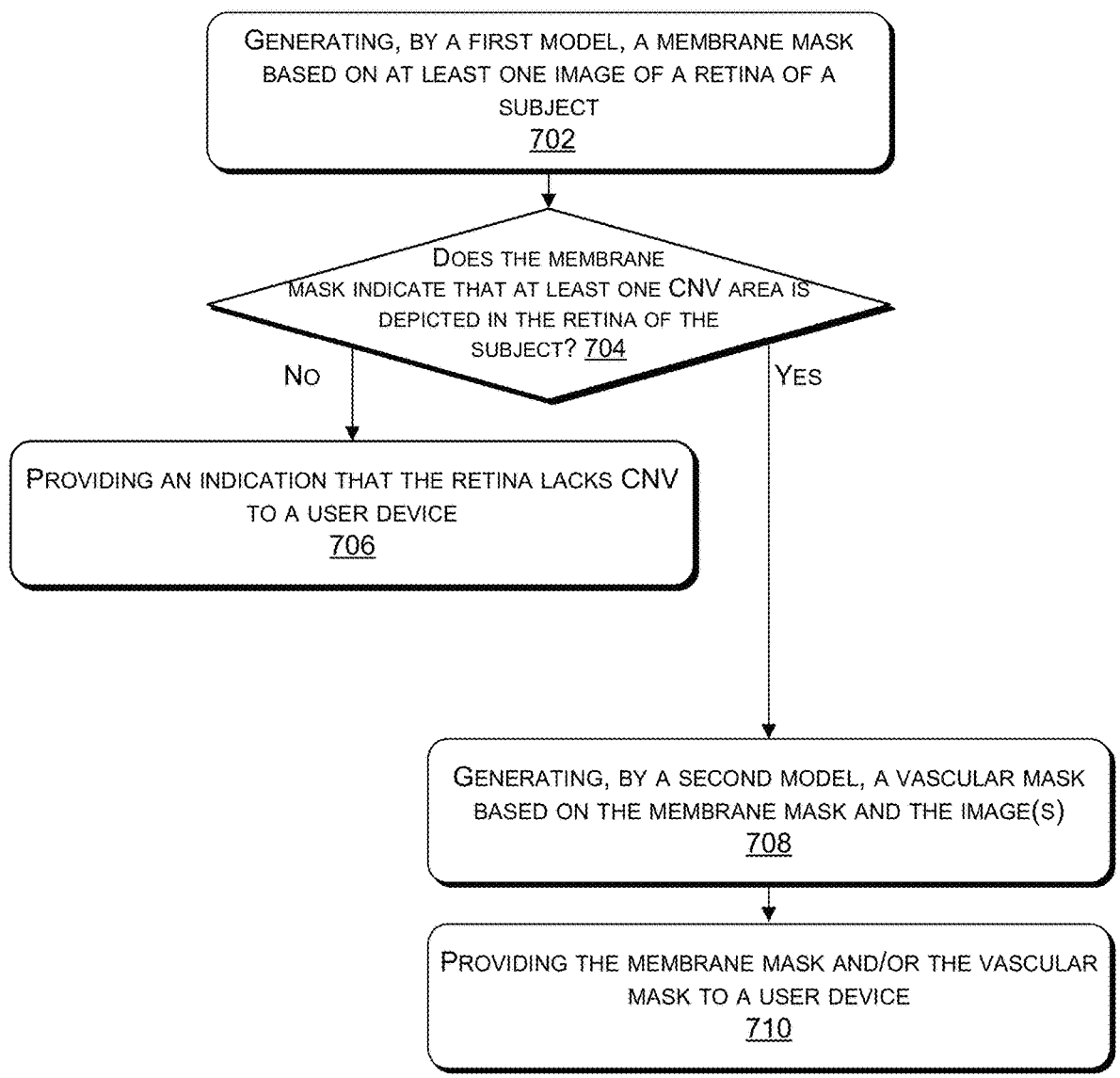
FIG. 7 illustrates an example process for identifying CNV in a subject.

FIG. 7 illustrates an example process 700 for identifying CNV in a subject. The process 700 may be performed by various entities described herein, such as at least one of the prediction system 102, predictive model 116, CNV membrane segmenter 118, or the CNV vessel segmenter 120 described above with reference to FIG. 1; the CNV membrane segmenter 300 described above with reference to FIG. 3; and/or the CNV vasculature segmenter 400 described above with reference to FIG. 4.

At 702, the process 700 includes generating, by a first model, a membrane mask based on at least one image of a retina of a subject. The membrane mask, for instance, may represent a location of at least one CNV membrane depicted in the image(s). For example, the membrane mask can be a probability map or a binary image with the same pixel dimensions (e.g., the same pixel height and pixel width) as the image(s), wherein each pixel of the membrane mask can indicate whether the corresponding pixel (at the same pixel location) in the image(s) depicts at least a portion of a CNV membrane. An example pixel of the probability map can be in a range of 0 to 1, and may represent a probability that the corresponding pixel of the image(s) depicts a part of a CNV membrane. An example pixel of the binary image may have a value of 0 or 1, wherein "0" indicates that the corresponding pixel in the image(s) does not depict any part of a CNV membrane and wherein "1" indicates that the corresponding pixel in the image(s) depicts at least a part of the CNV membrane. In various examples, the first model may include a NN, such as a CNN. The CNN may have been trained prior to 702, in various cases.

At 704, the process 700 includes determining whether the membrane mask indicates that at least one CNV area is depicted in the retina of the subject. According to some implementations, 704 includes determining whether any pixels of the probability map are above a particular threshold (e.g., 0.5). In some cases, 704 includes determining whether any pixels of the binary image are equal to one. According to some implementations, a size cutoff may be applied at 704. For example, 704 may include determining whether any groups of adjacent pixels in the membrane mask indicate the presence of a CNV membrane that exceeds a particular threshold size (e.g., a width and/or height threshold of pixels). Accordingly, the process 700 may be prevented from interpreting small artifacts (e.g., bulk motion artifacts) as CNV membrane areas.

If no CNV area is determined to be depicted in the retina of the subject at 704, the process 700 proceeds to 706. At 706, the process 700 includes providing an indication that the retina lacks CNV to a user device. In some cases, the indication can be output (e.g., displayed) on the user device. Accordingly, a clinician may utilize the identification to determine that the subject does not have CNV.

If, on the other hand, at least one CNV area is determined to be depicted in the retina of the subject at 704, the process 700 proceeds to 708. At 708, the process 700 includes generating, by a second model, a vascular mask based on the membrane mask and the image(s). The vascular mask, for instance, may represent a location of at least one vessel in the CNV membrane depicted in the image(s). For example, the vascular mask can be a probability map or a binary image with the same pixel dimensions (e.g., the same pixel height and pixel width) as the image(s), wherein each pixel of the vascular mask can indicate whether the corresponding pixel (at the same pixel location) in the image(s) depicts at least a portion of a vessel in the CNV membrane. An example pixel of the probability map can be in a range of 0 to 1, and may represent a probability that the corresponding pixel of the image(s) depicts a part of a vessel. An example pixel of the binary image may have a value of 0 or 1, wherein "0" indicates that the corresponding pixel in the image(s) does not depict any part of vessel and wherein "1" indicates that the corresponding pixel in the image(s) depicts at least a part of a vessel in the CNV membrane. In various examples, the second model may include a NN, such as a CNN. The CNN may have been trained prior to 708, in various cases.

At 710, the process 700 includes providing the membrane mask and/or the vascular mask to the user device. In some cases, the membrane mask and/or the vascular mask may be output (e.g., displayed) by a UI of the user device. According to some implementations, the membrane mask and/or the vascular mask may be overlaid with the image(s) (e.g., a PR-OCTA image) of the retina. Accordingly, a clinician may utilize the membrane mask and/or the vascular mask to identify, quantify, track, and/or diagnose CNV in the subject.

Figure 8:
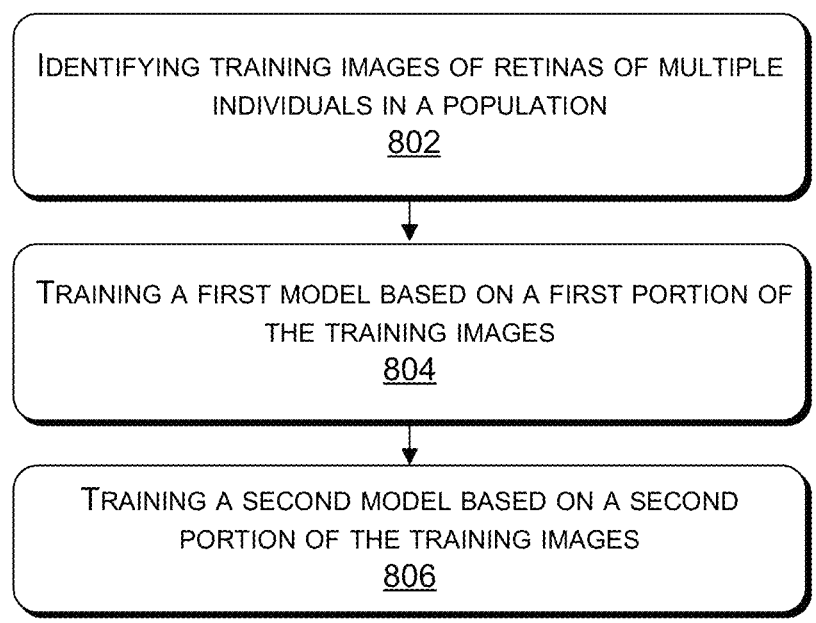
FIG. 8 illustrates an example process for training models to identify CNV in a subject.

FIG. 8 illustrates an example process 800 for training models to identify CNV in a subject. The process 800 can be performed by various entities described herein, such as at least one of the prediction system 102 or the trainer 104 described above with reference to FIG. 1.

At 802, the process 800 includes identifying training images of retinas of multiple individuals in a population. The multiple individuals may have different pathologies, demographics, and the like. In some cases, the training images may have different image qualities. For instance, at least some of the training images may depict artifacts, such as projection and/or bulk motion artifacts. According to some implementations, the training images may include angiographic images (e.g., OCTA images), volumetric images, and/or membrane masks identifying CNV membranes and/or vasculature in the angiographic images. In some cases, the membrane masks may be, for instance, manually segmented by expert graders.

At 804, the process 800 includes training a first model based on a first portion of the training images. According to some implementations, the first model may include a CNN with various parameters that are optimized based on the training images. The first model may be trained to identify CNV membrane areas in angiographic and/or volumetric retina images.

At 806, the process 800 includes training a second model based on a second portion of the training images. The first portion and the second portion may include at least some of the same images. According to some implementations, the second model may include a CNN with various parameters that are optimized based on the training images. The second model may be trained to identify vasculature in CNV membrane areas in angiographic and/or volumetric retina images. In various examples, the first and second models, once trained, can be used to identify CNV membranes and/or vasculature in images of retinas of subjects outside of the population.

Figure 9:
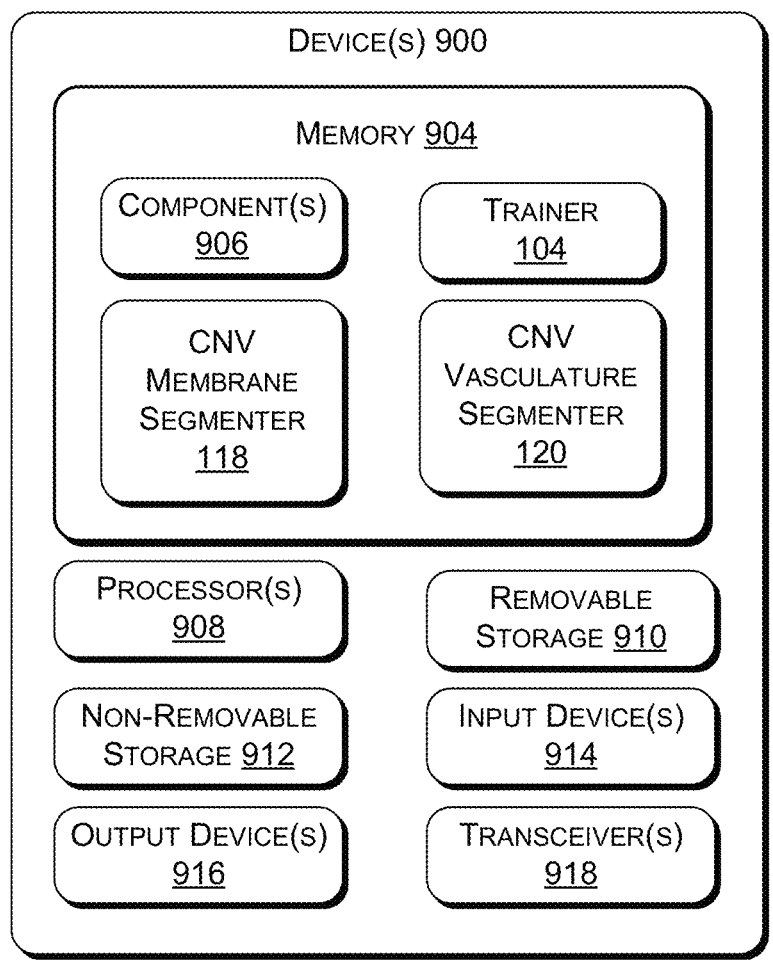
FIG. 9 illustrates an example of one or more devices that can be used to implement any of the functionality described herein.

FIG. 9 illustrates an example of one or more devices 900 that can be used to implement any of the functionality described herein. In some implementations, some or all of the functionality discussed in connection with FIGS. 1-8 can be implemented in the device(s) 900. Further, the device(s) 900 can be implemented as one or more server computers 902, a network element on a dedicated hardware, as a software instance running on a dedicated hardware, or as a virtualized function instantiated on an appropriate platform, such as a cloud infrastructure, and the like. It is to be understood in the context of this disclosure that the device(s) 900 can be implemented as a single device or as a plurality of devices with components and data distributed among them.

As illustrated, the device(s) 900 include a memory 904. In various embodiments, the memory 904 is volatile (such as RAM), non-volatile (such as ROM, flash memory, etc.) or some combination of the two.

The memory 904 may store, or otherwise include, various components 906. In some cases, the components 906 can include objects, modules, and/or instructions to perform various functions disclosed herein. The components 906 can include methods, threads, processes, applications, or any other sort of executable instructions. The components 906 can include files and databases. For instance, the memory 904 may store instructions for performing operations of any of the trainer 104, the CNV membrane segmenter 118, or the CNV vasculature segmenter 120.

In some implementations, at least some of the components 906 can be executed by processor(s) 908 to perform operations. In some embodiments, the processor(s) 908 includes a Central Processing Unit (CPU), a Graphics Processing Unit (GPU), or both CPU and GPU, or other processing unit or component known in the art.

The device(s) 900 can also include additional data storage devices (removable and/or non-removable) such as, for example, magnetic disks, optical disks, or tape. Such additional storage is illustrated in FIG. 900 by removable storage 910 and non-removable storage 912. Tangible computer-readable media can include volatile and nonvolatile, removable and non-removable media implemented in any method or technology for storage of information, such as computer readable instructions, data structures, program modules, or other data. The memory 904, removable storage 910, and non-removable storage 912 are all examples of computer-readable storage media. Computer-readable storage media include RAM, ROM, EEPROM, flash memory or other memory technology, CD-ROM, Digital Versatile Discs (DVDs), Content-Addressable Memory (CAM), or other optical storage, magnetic cassettes, magnetic tape, magnetic disk storage or other magnetic storage devices, or any other medium which can be used to store the desired information and which can be accessed by the device(s) 900. Any such tangible computer-readable media can be part of the device(s) 900.

The device(s) 900 also can include input device(s) 914, such as a keypad, a cursor control, a touch-sensitive display, voice input device, etc., and output device(s) 916 such as a display, speakers, printers, etc. In some implementations, the input device(s) 914, in some cases, may include a device configured to capture OCT images, such as OCTA images. In certain examples, the output device(s) 916 can include a display (e.g., a screen, a hologram display, etc.) that can display a PR-OCTA image of a retina of a subject overlaid with a predicted CNV membrane image and/or a predicted CNV vascular image, thereby identifying CNV in the retina of the subject.

As illustrated in FIG. 9, the device(s) 900 can also include one or more wired or wireless transceiver(s) 916. For example, the transceiver(s) 916 can include a Network Interface Card (NIC), a network adapter, a Local Area Network (LAN) adapter, or a physical, virtual, or logical address to connect to the various base stations or networks contemplated herein, for example, or the various user devices and servers. The transceiver(s) 916 can include any sort of wireless transceivers capable of engaging in wireless, Radio Frequency (RF) communication. The transceiver(s) 916 can also include other wireless modems, such as a modem for engaging in Wi-Fi, WiMAX, Bluetooth, or infrared communication.

Example: Automated Diagnosis and Segmentation of Choroidal Neovascularization in OCT Angiography Using Deep Learning Accurate identification and segmentation of CNV allows for the diagnosis and management of neovascular age-related macular degeneration (AMD). PR-OCTA enables both cross-sectional and en face visualization of CNV. This Example describes a novel technique that utilizes CNNs to perform automated retinal segmentation and CNV identification. This Example used a clinical data set, including both scans with and without CNV, and scans of eyes with different pathologies. The clinical data set included scans with various image qualities. As shown herein, the technique described in this Example has been validated on low image quality eye scans. During validation, the method successfully identified CNV and distinguished between scans depicting CNV and scans that did not depict CNV (i.e., non-CNV controls). Accordingly, this Example provides a fully automated categorization and segmentation technique that can be used to accurately diagnose, visualize, and monitor CNV.

Because PR-OCTA is non-invasive and images are acquired easily and rapidly in the clinical setting, PR-OCTA provides the opportunity to develop routine imaging for CNV detection and monitoring. Such monitoring allows early detection of CNV and conversion to exudative CNV, further allowing for successful intervention. Furthermore, improved quantification of CNV features can identify additional indicators for disease progression (M. Al-Sheikh et al., RETINA 38, 220-230 (2018)).

This Example provides an automated technique that utilizes CNNs to classify an input scan based on the presence or absence of a segmented CNV membrane. If CNV is present, the technique can further segment the CNV vasculature enclosed by the CNV. In this Example, two separate CNNs can be trained, as detailed below. These networks perform complimentary tasks, and together comprise a robust system for CNV characterization.

Data Acquisition and Pre-Processing

OCTA datasets with a large range of signal strength index (SSI) were collected from the retina clinics at the Casey Eye Institute, Oregon Health & Science University, Portland, OR, USA and Shanxi Eye Hospital, Taiyuan, Shanxi, PR China. These datasets were obtained in compliance with the Declaration of Helsinki.

Subjects were scanned using a 70-kHz commercial OCTA system (RTVue-XR; Optovue, Fremont, CA) with a central wavelength of 840 nm. The scan area was 3×3-mm and centered on the fovea. Two repeat B-scans were collected from each subject at the same position. Retinal flows were detected using the commercial split-spectrum amplitude-decorrelation angiography (SSADA) algorithm (Y. Jia et al., Optics Express 20, 4710-4725 (2012)). One X-fast and one Y-fast scan were obtained from each subject and registered to suppress motion artifacts. Scans from subjects with CNV secondary to neovascular AMD were utilized in this example. Subjects whose eyes were without CNV (e.g., "control eyes") included eyes with non-neovascular AMD, diabetic retinopathy (DR), branch retinal vein/artery occlusion (BRVO/BRAO), central serous chorioretinopathy (CSC), and healthy eyes. No scans were excluded due to low image quality.

Various scans were input into a CNN model. Scans input into the CNN model included several en face images, each of which was useful for CNV identification or segmentation in some capacity. The en face retinal angiograms were generated using anatomic slab segmentation. In this Example, anatomic slab segmentation was accomplished using a semi-automatic approach based on graph search implemented in a previously published OCTA processing toolkit (M. Zhang et al., Biomedical Optics Express 6, 4661-4675 (2015); Y. Guo et al., Biomedical Optics Express 9, 4429-4442 (2018)). Further, segmentation of the inner limiting membrane (ILM), outer border of the outer plexiform layer (OPL), and Bruch's membrane (BM) was used to construct inner and outer retinal images (See FIG. 10). In this Example, the "inner retina" is defined as the portions of the retina defined between the ILM and the OPL, and the "outer retina" is defined as the portions of the retina defined between the OPL and the BM. Input images included uncorrected original inner and outer retinal en face angiograms, as well as slab-subtracted and projection-resolved outer retinal angiograms (FIG. BA-BH) (for examples of slab-subtracted angiograms, see L. Liu et al., Biomedical Optics Express 6, 3564-3576 (2015); Y. Jia et al., Ophthalmology 121. 1435-1444 (2014); Y. Jia et al., PNAS 201500185 (2015)). These types of images were found to be valuable for artifact removal. PR-OCTA achieves relatively high quality angiograms in the outer retina, but some residual projection artifacts can remain that could be confused for CNV. Slab-subtraction was utilized for projection artifact removal, wherein flow signals from superficial slabs were subtracted from deeper slabs in the retina. A slab-subtracted image is defined as an original outer retinal image subtracted by the product of an original retinal image and $\alpha$, wherein the original outer retinal image and the original retinal image depict the same retina, and $0<\alpha<1$. Compared to the original PR-OCTA images, slab-subtraction images retain fewer regions with spurious signals. However, true vessels may be interrupted or erased in slab-subtraction, which can disrupt vascular morphology. Original uncorrected angiograms of the outer retina may have the opposite problem, as the uncorrected angiograms can be projection artifact-rich, with false flow pixels mimicking superficial vasculature. Including all four of these types of angiograms (original inner and outer angiograms, slab-subtracted outer retina, and projection-resolved outer retina) allowed the CNN model to efficiently differentiate artifacts from true signal. For example, the original angiograms can be used to corroborate the location of false flow, the slab-subtracted angiograms can be used to identify regions with a high probability of including CNV, and the PR angiograms can provide excellent image quality in the region containing CNV.

Figure 10:
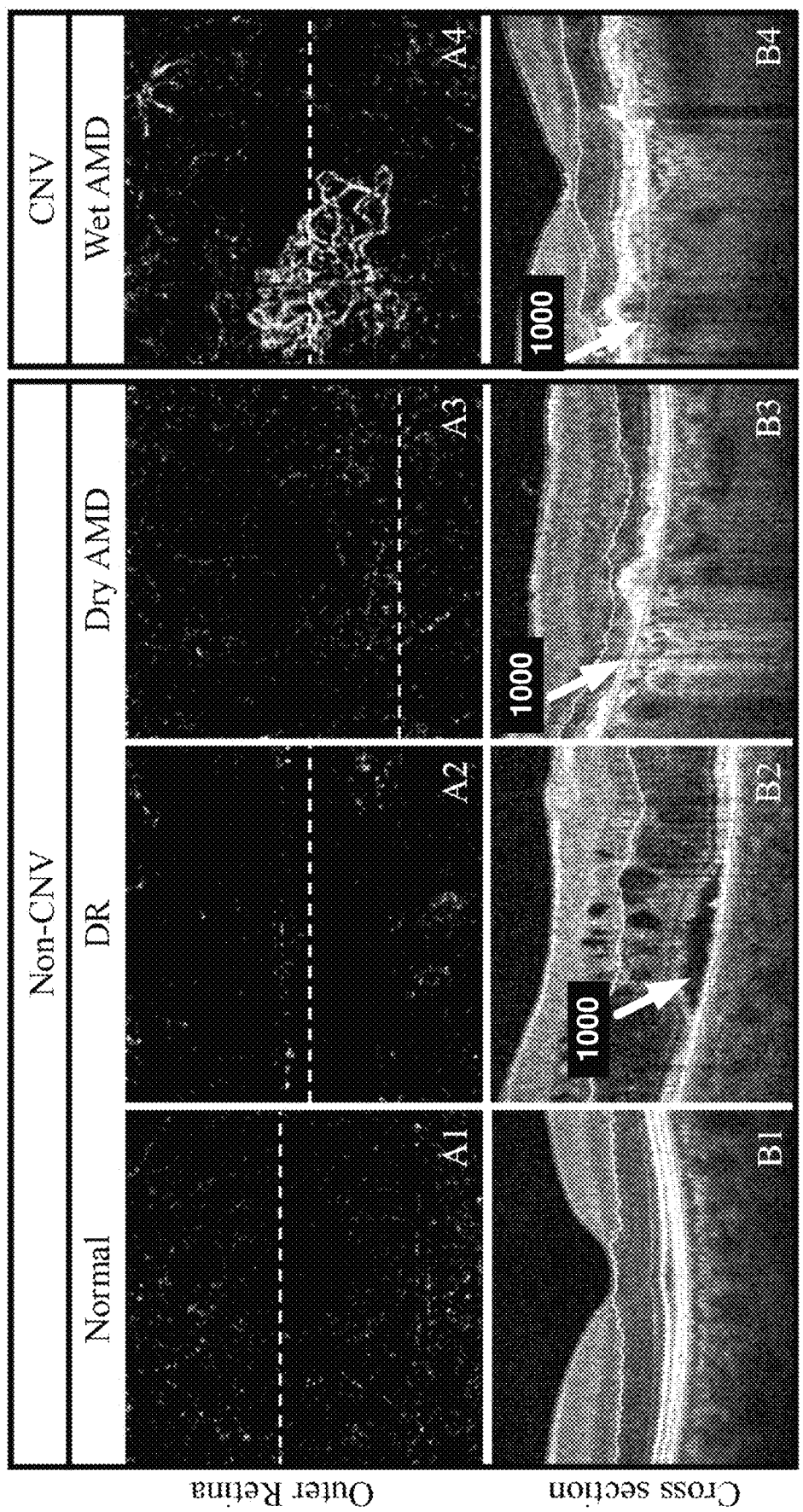
FIG. 10 illustrates a series of images depicting examples of outer retinal structural volumes.

FIG. 10 illustrates a series of images depicting examples of outer retinal structural volumes that were included in the CNN model input. Notably, in this Example, the reliance on outer retinal structural volumes was used to reduce computational budget and memory cost of the associated computer-based evaluations. However, in other implementations, whole retina images (e.g., inner retinal structure volumes, outer retinal structure volumes, combinations of inner and outer retinal structure volumes, or whole OCT volumes (e.g., volumes depicting both retinal and choroidal structures). As shown in FIG. 10, CNV appears in the examples along with the elevation of RPE. Thus, slab subtraction facilitates artifact removal in regions where the RPE is in normal (part B1), detached (part B2) or lost (part B3) states. To generate the outer volumes with the same size, A-lines in the outer slab were resized to a voxel depth for data alignment (see, e.g., FIG. 12). FIG. 10 illustrates a comparison of non-CNV, including a healthy (parts A1 and B1), diabetic retinopathy (DR, parts A2 and B2), and dry AMD (parts A3 and B3), and CNV (wet AMD, Parts A4 and B4) scans with en face outer retinal angiograms (parts A1 to A4) and cross-sectional structural OCT overlaid with OCTA (parts B1 to B4) showing inner retinal (violet), choroidal (red), and pathological outer retinal flow (yellow). Slab segmentation lines are the inner limiting membrane (violet), outer border of the outer plexiform layer (yellow), and Bruch's membrane (green). White dotted lines in parts A1 to A4 of FIG. 10 indicate the locations of the cross sections in FIG. 10. Red arrows indicate the pathologies 1000 in outer retina.

Figure 11:
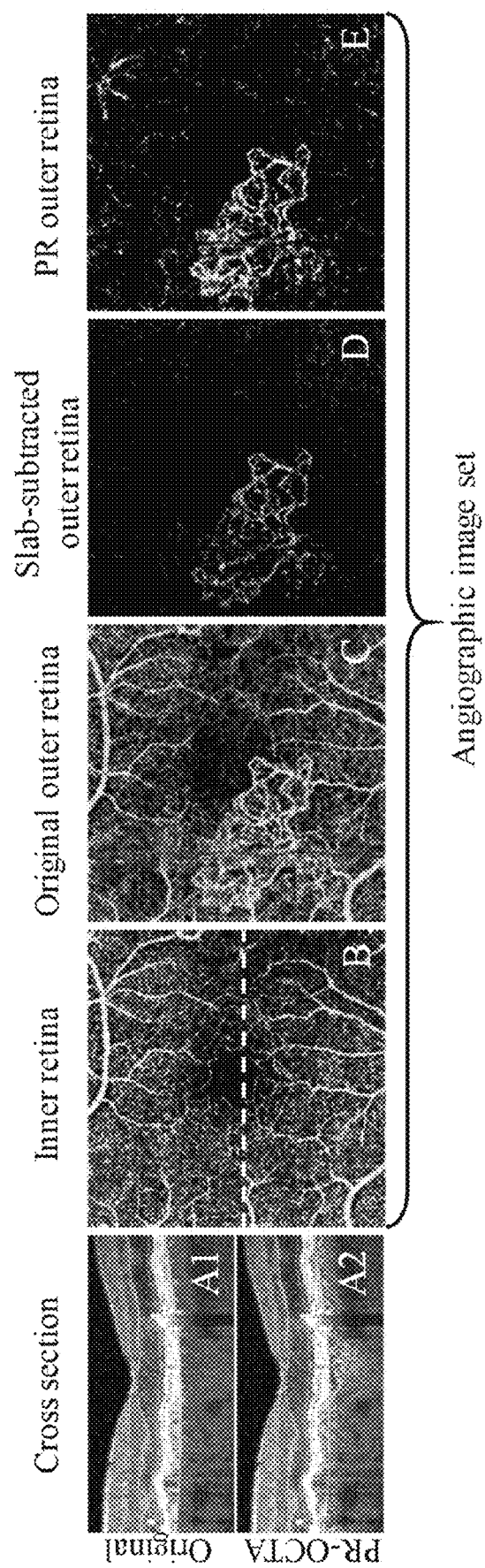
FIG. 11 illustrates an example input angiographic image set that includes original (and projection-resolved (PR) OCTA with inner retinal, choroidal, and outer retinal flow overlaid on structural OCT.

FIG. 11 illustrates an example input angiographic image set that includes original (part A1) and projection-resolved (PR) OCTA (part A2) with inner retinal (violet), choroidal (red), and outer retinal (yellow) flow overlaid on structural OCT. Part B of FIG. 11 illustrates inner retinal angiogram, with white dotted line indicating the position of the B-scans in parts A1 and A2. Part C of FIG. 11 illustrates outer retinal angiogram generated from the original OCTA demonstrated in part A1. Part D of FIG. 11 illustrates outer retinal angiogram processed by slab subtraction. Part F of FIG. 11 illustrates PR-OCTA outer retinal angiogram. In part F, the CNV is preserved but some residual projection artifacts persist.

Figure 12:
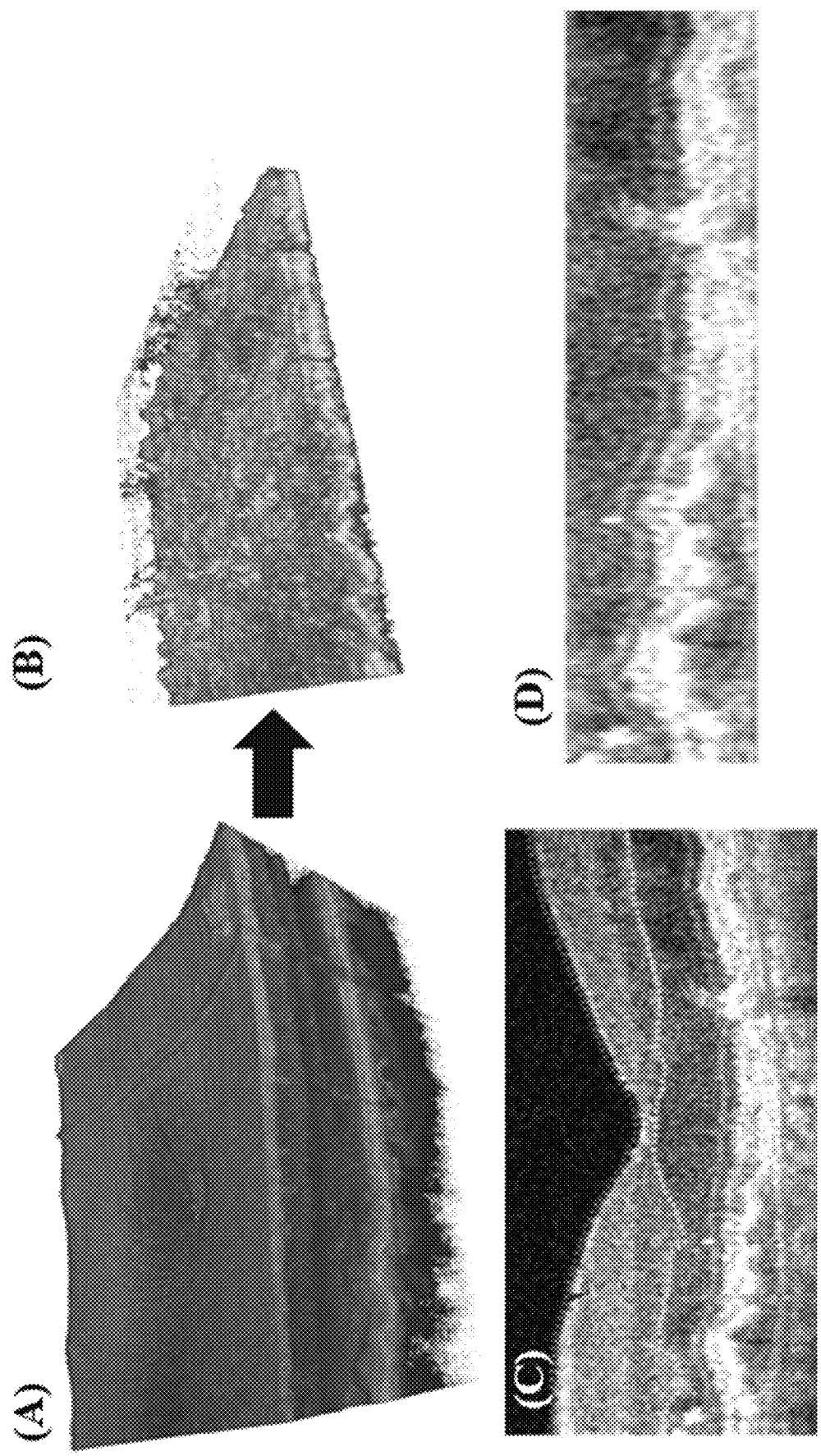
FIG. 12 illustrates an example a generated outer retinal structural volume input.

FIG. 12 illustrates an example a generated outer retinal structural volume input. Part A of FIG. 12 illustrates an original structural OCT volume obtained from a subject. Part B of FIG. 12 illustrates extracted outer retinal volume of the subject. Part C of FIG. 12 illustrates original cross-sectional OCT of the subject, with anatomic slab segmentation overlaid in violet (inner limiting membrane, ILM), yellow (outer plexiform layer, OPL), and green (Bruch's membrane, BM). Part D of FIG. 12 illustrates segmented outer retinal cross section of the subject, resized so that the volume has a constant voxel depth.

CNV Identification and Segmentation Using Convolutional Neural Networks

Using the CNN model, CNV was identified based at least on the presence of a CNV membrane. In this Example, the CNV membrane is defined as the damaged tissue mass within outer retina where CNVs grow into. CNV vessels were further segmented based on identified CNV scans.

Challenges

Figure 13:
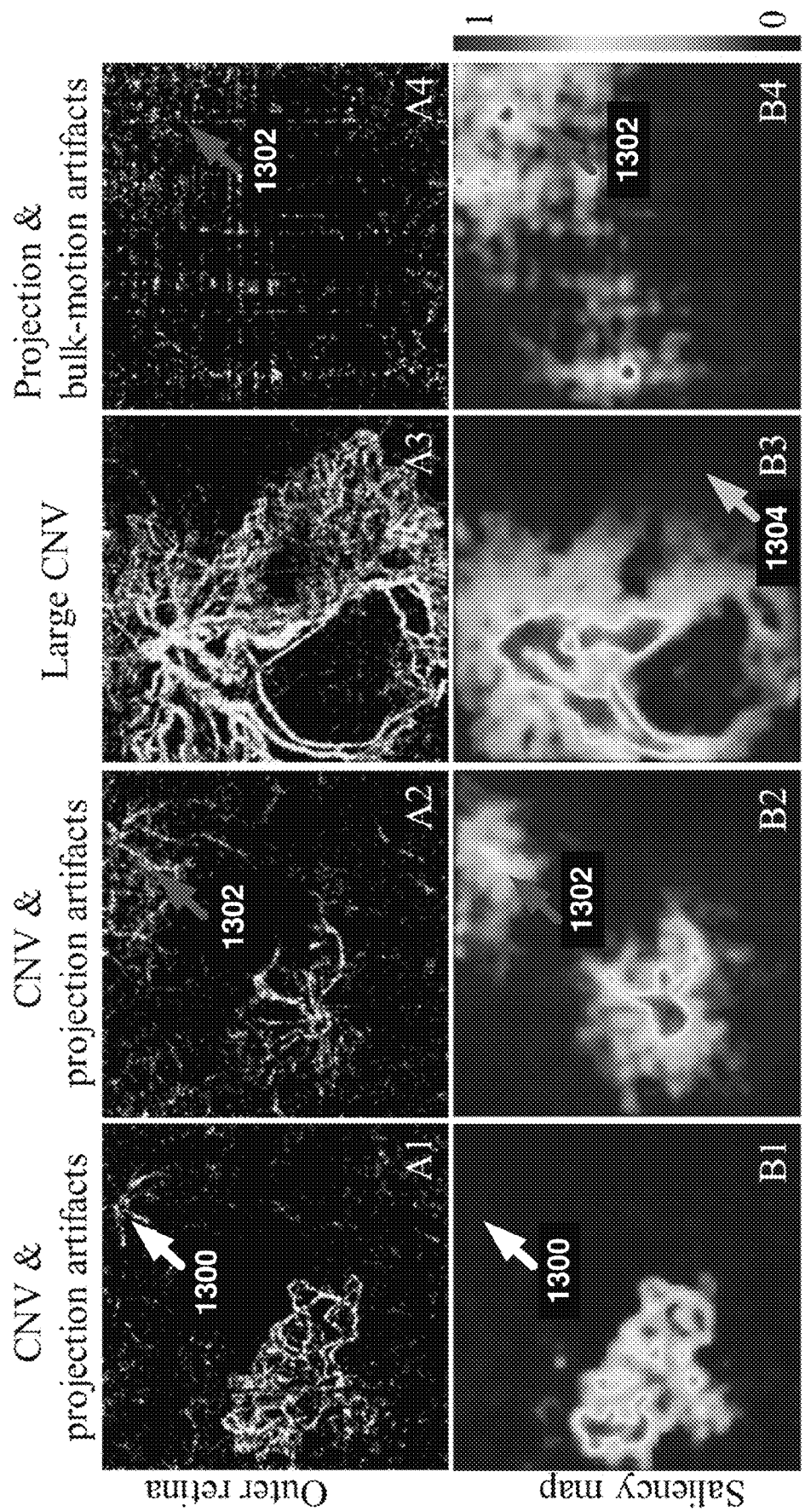
FIG. 13 illustrates CNV segmentation on challenging scans (i.e., scans with various artifacts) using the previously developed saliency-based algorithm.

CNV segmentation using en face outer retinal angiograms can be compromised by a variety of image features, including residual projection and motion artifacts, as well as background noise. FIG. 13 illustrates CNV segmentation on challenging scans (i.e., scans with various artifacts) using the previously developed saliency-based algorithm. Small residual projection artifacts 1300 are excluded in the saliency map (parts A1 and B1, highlighted by white arrows). Strong residual artifacts in CNV and non-CNV scans were over-detected in the saliency map, providing false positives 1302 (parts A2, B2, A4, and B4, highlighted by red arrows), while large CNV was under-detected in the saliency map, producing false negatives 1304 (Parts A3 and B3, indicated by green arrows). On scans where artifacts are small and have lower signal than the CNV, the previous saliency-based algorithm was capable of segmenting the CNV properly (parts A1 and B1). However, on scans where the area and signal of residual artifacts are similar to the CNVs, the algorithm readily kept false positives on the saliency map (parts A2 and B2). Since the saliency-based algorithm is configured to segment CNV based on the degree of saliency, larger CNV vessels with strong signal are easier to separate from artifacts than smaller CNV vessels. In cases with very large CNV, the large thick CNV vessels have a much higher flow signal than the smaller CNV capillaries and the saliency-based algorithm mistakenly segments these smaller vessels as background (parts A3 and B3). In a non-CNV control cases, an accurate automated CNV detection algorithm ignores the background noise instead of segmenting false positives. The previous saliency algorithms also fail in this case (parts A4 and B4). In contrast, the CNN model provided in this Example successfully overcame these limitations.

CNN Model Outline

Figure 14:
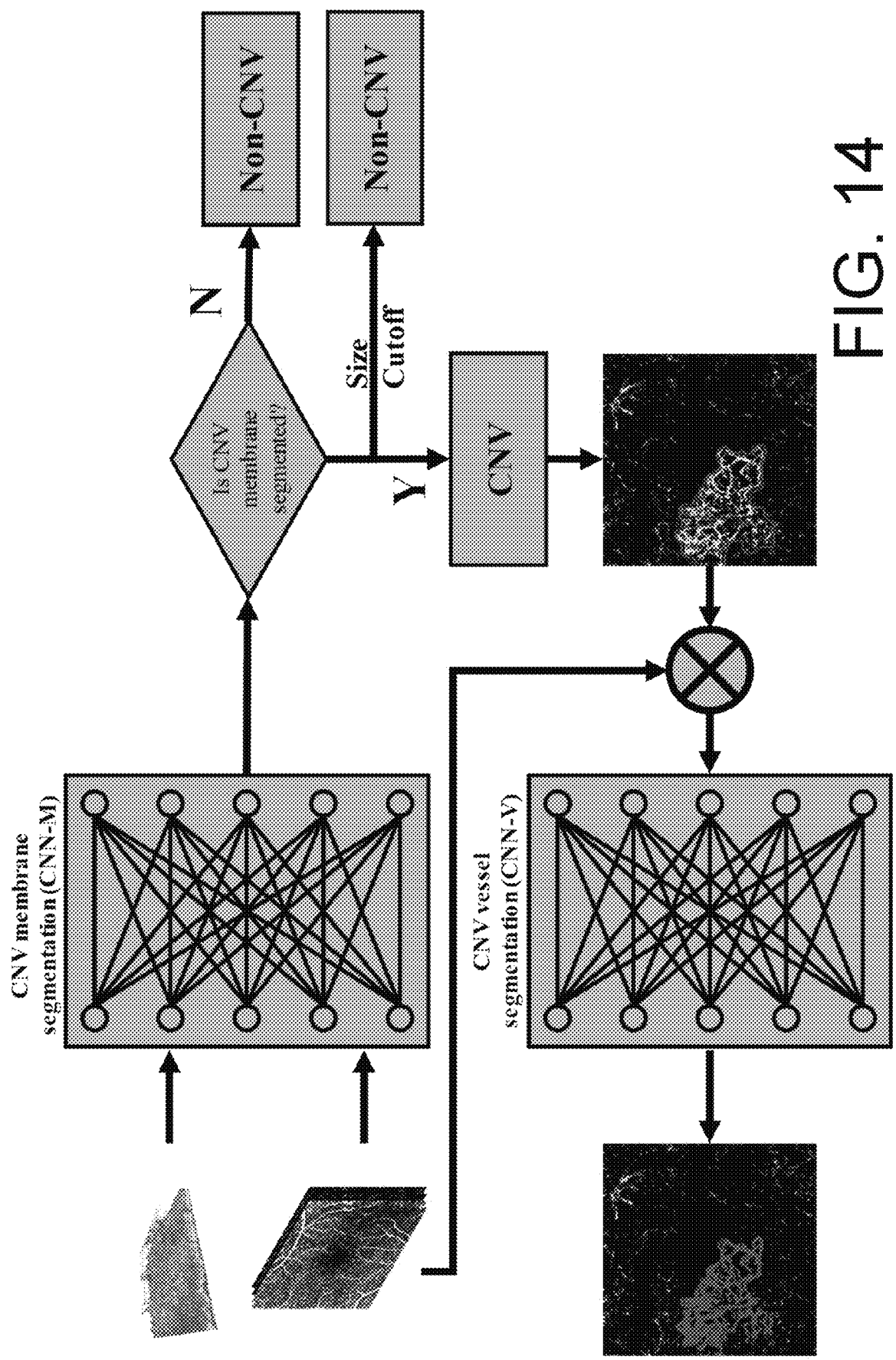
FIG. 14 illustrates an outline of a proposed automated CNV identification and segmentation method.

The CNN model utilized in this Example includes two CNNs: a first CNN trained to perform CNV membrane identification and segmentation (CNN-M) and a second CNN trained to perform pixel-wise vessel segmentation (CNN-V). FIG. 14 illustrates an outline of the proposed automated CNV identification and segmentation method. Inputs to the CNN model can include the original inner retinal angiogram and original, slab-subtracted, projection-resolved (PR) outer retinal angiograms, and volumetric structural data from the outer retina. The first CNN (CNN-M) is configured to segment a CNV membrane and output a mask corresponding to a location of the CNN membrane (if present). The second CNN (CNN-V) is configured to segment CNV vascular pixels within the CNV membrane output by the first CNN.

As shown in this Example, the CNN model depicted in FIG. 14 was utilized to identify and segment CNV in a subject using the following example data pipeline. First, both the structural and angiographic image sets of the subject were input into the first CNN for CNV membrane segmentation. If the first CNN did not detect the presence of CNV, the first CNN is configured to classify the image sets of the subject as CNV-free. However, in some cases, a residual artifact in the image sets may appear similarly to the first CNN as CNV. Since the interference of residuals is likely, a size cutoff threshold, which can be estimated by maximizing the identification sensitivity in a training dataset, can be applied. In this Example, a size cutoff threshold of 0.004 $mm^2$ (or the corresponding area of pixels) was used. Accordingly, the cutoff threshold can prevent the first CNN is from incorrectly classifying the residual artifact as CNV. If the first CNN detects the presence of CNV, the first CNN outputs an image representing a segmented CNV membrane. The PR outer retinal angiogram can be multiplied (pixel-by-pixel) by the segmented CNV membrane probability map to suppress interference from the background. Next, the structural volume, angiographic image set, and CNV membrane probability weighted PR outer retinal angiogram can be input into the second CNN, which may perform CNV vessel segmentation. The second CNN may output an image representing the CNV vessel segmentation, which may be used by a clinician to accurately diagnose the presence and/or severity of CNV in the subject.

CNV Membrane Segmentation Using CNN

The CNN model of this Example utilized repeated pooling layers to enhance image classification. Repeated pooling layers can be used in many image processing networks. The repeated pooling layers can be beneficial to image classification in order to compress the key information for decision-making and extract features across different scales. However, the width of CNV vessels can be as small as just a single pixel. Repeated pooling layers may be problematic because the pooling layers decrease feature resolution and therefore may remove thin vessels. To preserve feature resolution while maintaining segmentation across multiple scales, one alternative is using larger size kernels. With this approach, however, the memory and computational cost would be overly burdensome. Instead, this Example utilizes a network design that replaced most pooling layers with atrous kernels in the convolutional layers (Chem G., arXiv preprint arXiv, 1706.05587 (2017); Chen. G. et al., IEEE Transactions on Pattern Analysis and Machine Intelligence 40, 834-848 (2018)). Atrous kernels of this Example dilated 3×3 kernels by inserting zeros between the kernel elements. The atrous kernel with size 1 is the original 3×3 kernel, while inserting one zero between the elements creates an atrous kernel of size two, and the atrous kernel with size 3 is created by inserting two zeros (etc.). As the size of the atrous kernel increases, the field of view is enlarged, but the memory and computational cost is nonetheless equivalent to the original 3×3 kernel.

Figure 15:
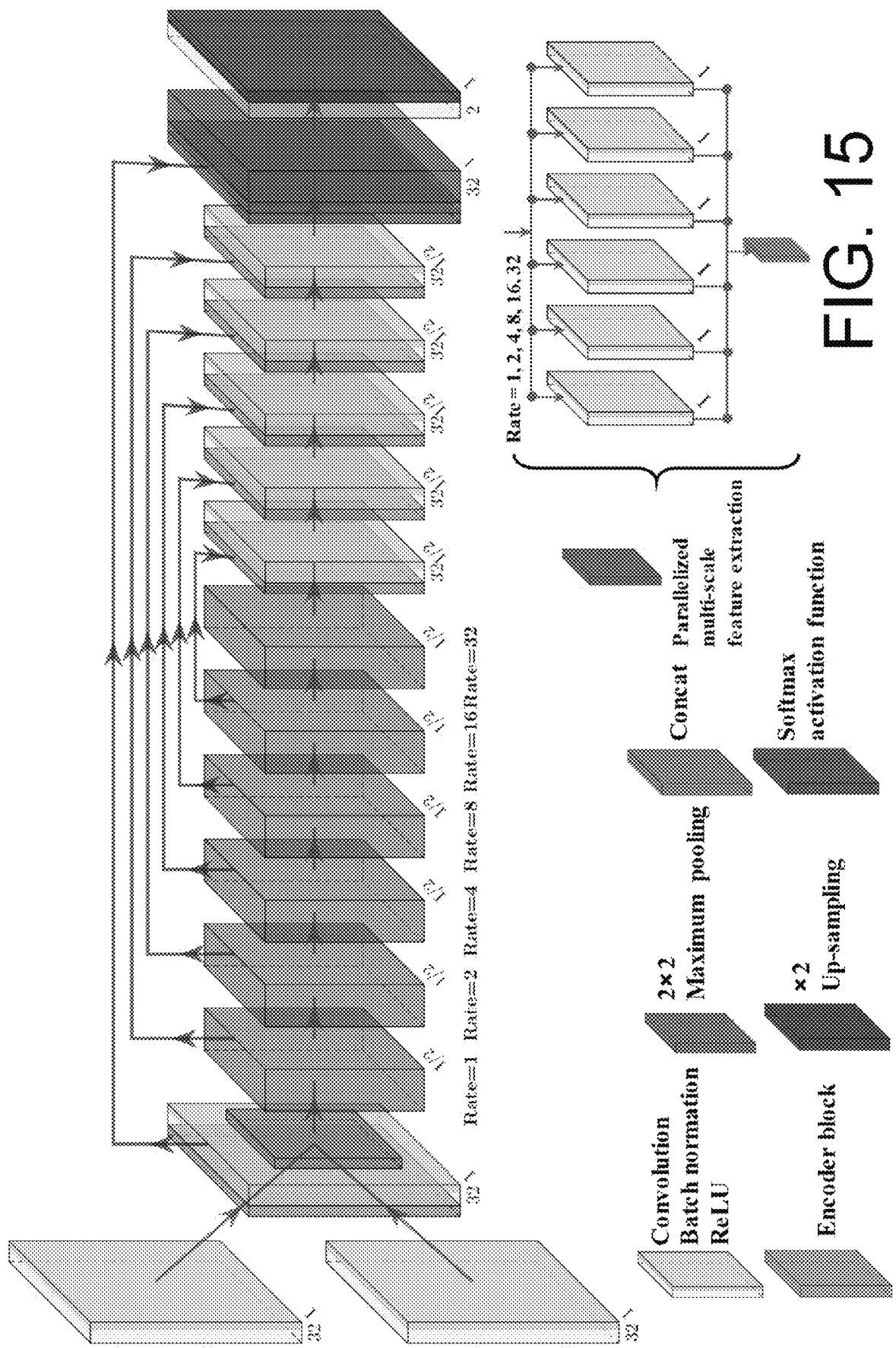
FIG. 15 illustrates the CNN architecture for a CNN that performs CNV membrane segmentation.

The first and second CNNs in the CNN model were designed to have different CNN architectures. FIG. 15 illustrates the CNN architecture for the first CNN, which performs CNV membrane segmentation (CNN-M). The atrous kernel sizes (Rate=1 to 32) are annotated below each encoder block. The number of kernels is annotated below each convolutional layer. Labels I or I/2 under various blocks indicate whether the corresponding blocks performed operations on the full and half-sized image, respectively.

The first CNN (FIG. 15) was configured to extract features in the structural volume and angiographic image set, respectively. The following concatenation and convolutional layers in the first CNN merged the structural and angiographic features, and then input the merged features into the encoder blocks for feature extraction. The first CNN includes a single pooling layer after feature merging. The encoder block was designed using atrous kernels, and the dilation rate increased in deeper layers. To make the best of low-level features and to transmit the loss from deeper to shallower layers, a U-net like architecture was applied in the decoder section. Moreover, the decision-making layer was parallelized using atrous kernels to refer features in multi-scales, with the atrous kernel dilation rates varying from 1 to 32, increasing by multiples of 2. A softmax activation layer was able to output the CNV membrane probability map.

Figure 16:
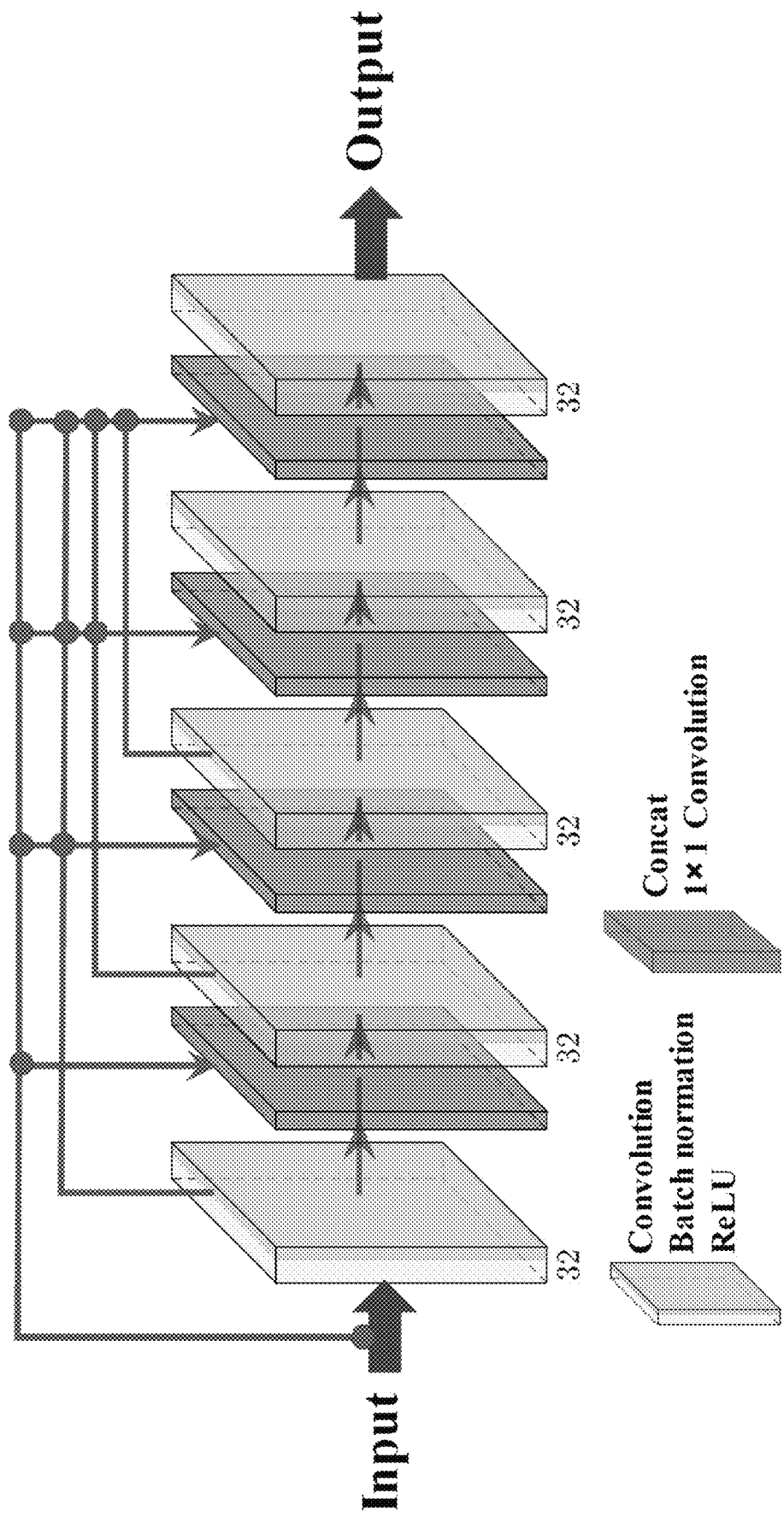
FIG. 16 illustrates an encoder block architecture utilized in an example CNN model.

Since the pooling layers were replaced with atrous kernels, the number of kernels in encoder and decoder layers was fixed at 32 in this Example to accommodate memory considerations. A densely connected CNN structure (modified to include atrous kernels) was applied in the encoder blocks, and features at low levels were concatenated to deeper levels (FIG. 15) (for an example of the densely connected CNN structure, see, e.g., G. Huang et al., PROCEEDINGS OF THE IEEE CONFERENCE ON COMPUTER VISION AND PATTERN RECOGNITION, 4700-4708 (2017)). The dilation rate of each encoder block varied, as demonstrated in FIG. 15. FIG. 16 illustrates the encoder block architecture utilized in the first CNN (and the second CNN) of the CNN model. The number of kernels is annotated below each convolutional layer. Dots at intersections along the lines indicate connections between layers.

CNV Vessel Segmentation Using CNN

The first CNN was configured to output a membrane probability map. The membrane probability map can be used to generate a binary image wherein each pixel has a first value (representing a potential CNV membrane area) or a second value (representing areas outside the potential CNV membrane area). In this Example, pixels with probabilities (of being part of a CNV membrane area) that were higher than 0.5 were identified as belong to the CNV membrane area. The primary task (locating the mask) of the first CNN is reliant on detection across multiple scales, a challenge distinct from vessel segmentation (since vessels mostly vary between 1 and 5 pixels in width).

Figure 17:
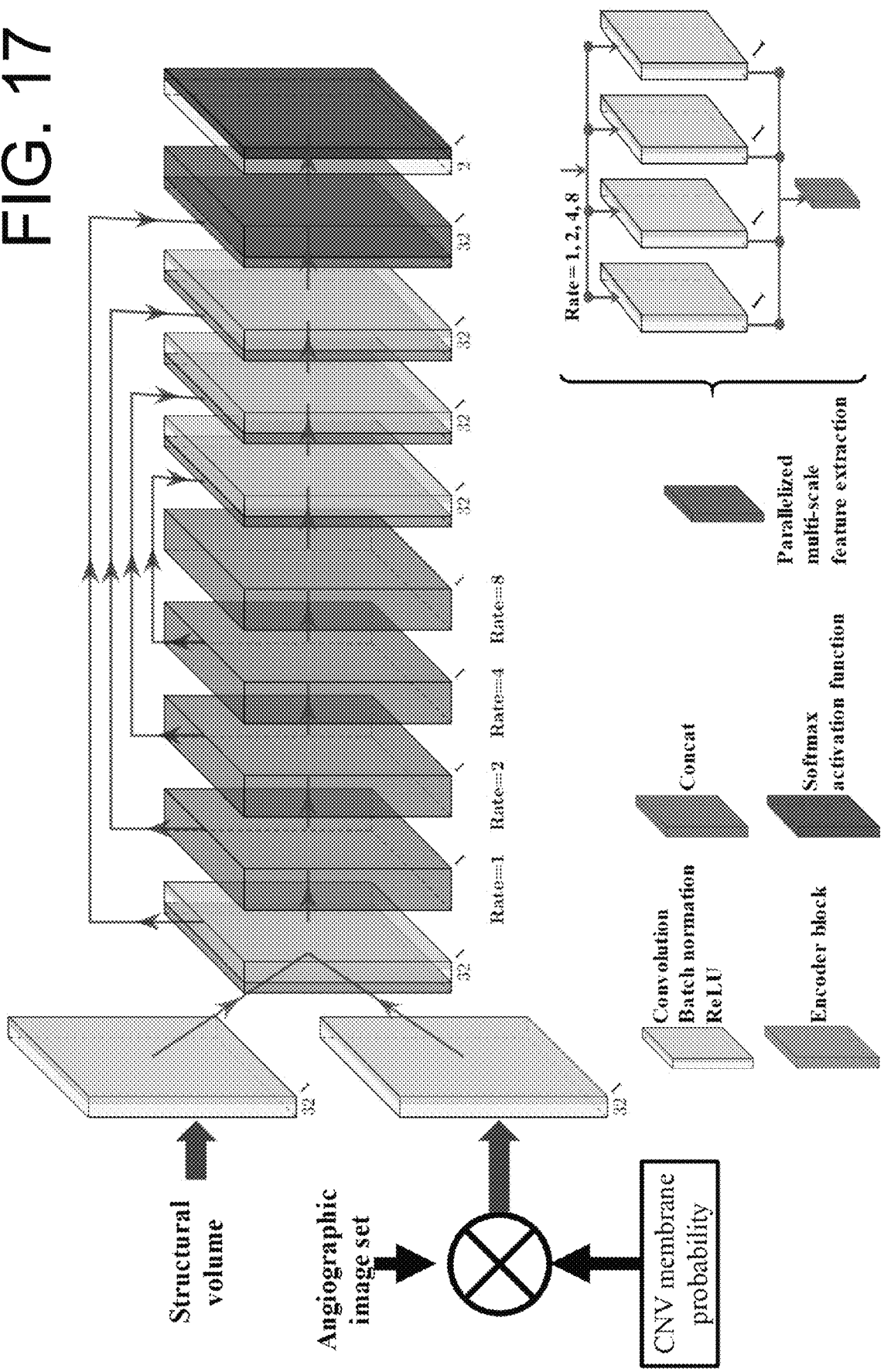
FIG. 17 illustrates the CNN architecture for a CNN that performs CNV vessel segmentation.

FIG. 17 illustrates the CNN architecture for the second CNN, which performs CNV vessel segmentation (CNN-V). The atrous kernel sizes (Rate=1 to 8) are annotated below each encoder block. The number of kernels is annotated below each convolutional layer. The label beside each block indicates the image size (e.g., a pixel dimension) of an input image to the block; in this case, the input to the second CNN is a fully-sized image. The architecture for the first CNN depicted in FIG. 15 was more complex than the architecture utilized for the second CNN depicted in FIG. 17, due to the differences between the tasks of membrane and vessel segmentations. Unlike the first CNN, the second CNN in FIG. 17 omitted the pooling layers in the feature merging section to keep the resolution sufficient to detect any CNV vessel (which may, e.g., have widths between 1 and 5 pixels). The dilation rates of the atrous kernels in the second CNN depicted in FIG. 17 were also smaller (e.g., rates=1, 2,4,8) in the encoder and decision-making blocks than the dilation rates of the first CNN depicted in FIG. 15.

Training

Training Dataset

The training dataset used to train the CNN model of this Example included both CNV and non-CNV control cases. The CNV patients were diagnosed by retinal specialists, with CNV due to AMD visible using PR-OCTA. The non-CNV control cases consist of healthy eyes and other retinal diseases including non-neovascular AMD, diabetic retinopathy (DR), branch retinal vein/artery occlusion (BRVO/BRAO), and central serous chorioretinopathy (CSC). A total of 1676 scans were collected, including repeated and follow-up scans. No scan was excluded due to low image quality. The datasets used for training and testing are completely from different eyes and are listed in Table 1.

TABLE 1

Dataset for training and testing

| | Training | | Testing | |
|---|---|---|---|---|
| | CNV | Non-CNV | CNV | Non-CNV |
| Eyes/Scans | 65/764 | 430/802 | 50/50 | 60/60 |

Ground Truth

Figure 18:
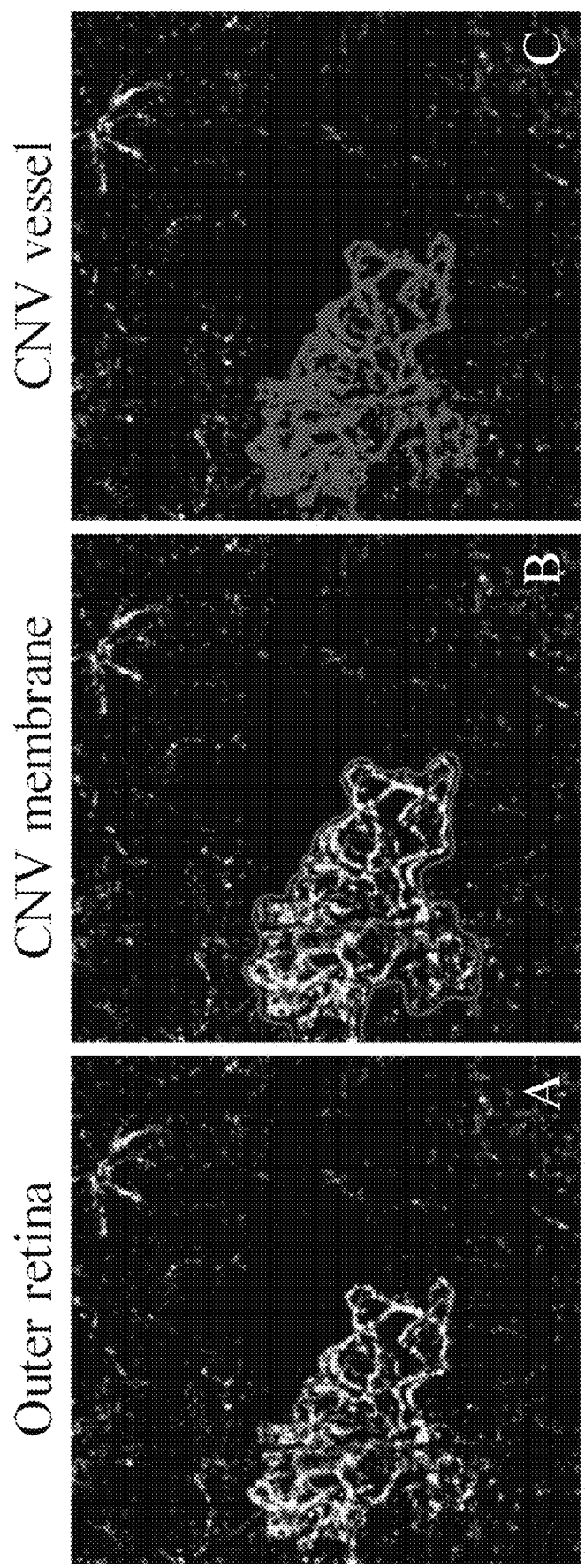
FIG. 18 illustrates an example of outer retina and segmented CNV membrane and vessel images utilized in a training set.

FIG. 18 illustrates an example of outer retina and segmented CNV membrane and vessel images utilized in the training set. Part A illustrates an outer retina angiogram generated form projection resolved (PR)-OCTA. Part B illustrates a CNV membrane outline drawn by an expert grader. Part C illustrates a CNV vessel mask verified by an expert grader.

A certified grader manually segmented the ground truth CNV membrane used in training. For this purpose, this Example utilizes PR outer retinal angiograms including relatively few projection artifacts. To exclude any remaining artifacts, the grader also referred to the uncorrected original angiograms of the inner and outer retina. For small CNV in low quality scans, B-scans were also reviewed to confirm the CNV position. The CNV membrane area was manually delineated (part B of FIG. 18). The Otsu algorithm with manual correction was applied in the graded CNV membrane area to generate the ground truth of CNV vasculatures (part C of FIG. 18).

Results

CNV Diagnostic Accuracy

A highly sensitive algorithm for CNV identification is desirable because missed CNV may result in vision loss that is otherwise treatable. Likewise, high specificity is also desirable for not mistakenly identifying CNV in non-CNV eyes. However, some residual artifacts are inevitable, and may mimic the appearance of CNV and so be erroneously segmented. This Example includes a cutoff value for CNV membrane area that increases the identification sensitivity to reduce false negative diagnoses. Scans with CNV membrane areas smaller than 0.004 mm$^2$, which is equivalent to 49-pixel area in image, were not considered to contain CNV in this Example. The sensitivity and specificity on the test data were 100% and 95%, respectively (Table 2), indicating that this Example included zero missed diagnoses for this dataset. The area under receiver operating characteristic curve (AROC) is 0.997, which demonstrates reliable diagnostic performance.

TABLE 2

CNV diagnostic accuracy

| CNV membrane area (cutoff value) | Sensitivity | Specificity |
|---|---|---|
| 0.004 mm$^2$ | 100% | 95% |

CNV Segmentation Accuracy

The CNV membrane segmentation accuracy was evaluated by intersection over union (IOU), precision, recall, and F1 score, which are defined by the following Equations 4 through 7:

$$IOU = \frac{GT \cap Out}{GT \cup Out} \quad (4)$$

$$precision = \frac{TP}{TP + FP} \quad (5)$$

$$recall = \frac{TP}{TP + FN} \quad (6)$$

$$F1 = 2 \times \frac{precision \times recall}{precision + recall} \quad (7)$$

where GT is the manually graded CNV membrane and Out is the CNV membrane area segmented by the proposed algorithm. TP is true positive, FP is the false positive, and FN is false negative. Overall, the algorithm achieved high scores in each of these metrics (Table 3).

TABLE 3

Agreement between CNV membrane outputs and ground truth (mean ± std)

| Mean Intersection over union (mIOU) | Precision | Recall | F1 score |
|---|---|---|---|
| 0.88 ± 0.10 | 0.95 ± 0.03 | 0.93 ± 0.11 | 0.93 ± 0.08 |

Figure 19:
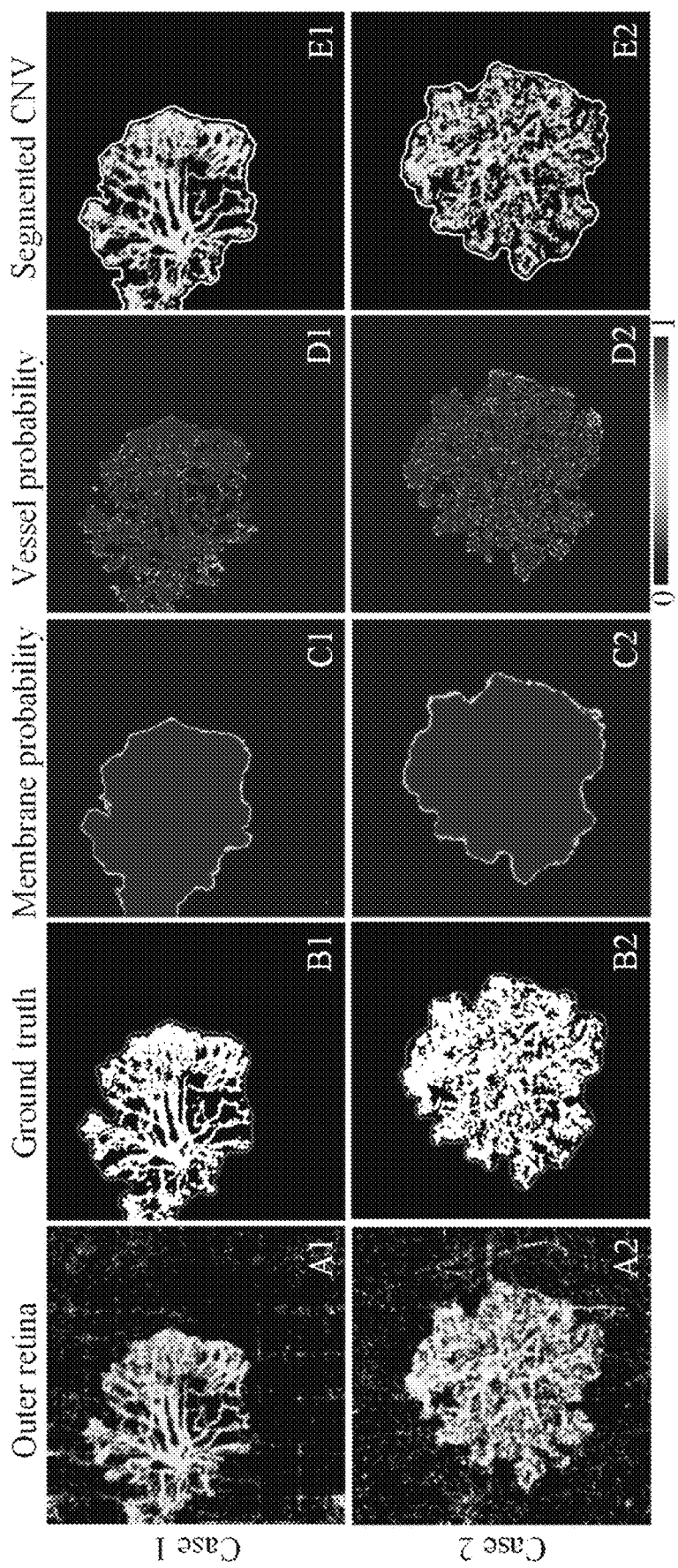
FIG. 19 illustrates CNV segmentation on scans with relatively good image quality.

FIG. 19 illustrates CNV segmentation on scans with good image quality. Parts A1 and A2 illustrate Projection-resolved (PR) outer retinal angiograms. Parts B1 and B2 illustrate manually delineated CNV membrane (red outline) and vessel (white pixels) ground truths; parts C1 and C2 illustrate probability maps output by the (first) membrane segmentation CNN (CNN-M); parts D1 and D2 illustrate probability maps output by the (second) vessel segmentation CNN (CNN-V); parts E1 and E2 illustrate a segmented CNV membrane (white outline, with probability>0.5) and vessels (with pixels of probability>0.5).

In order to better elucidate these results, this Example includes the proposed algorithm's performance on several exemplar scans exhibiting a variety of features. In the scans with clear CNV vasculature and minor artifacts (parts A1 and A2 of FIG. 19), the CNV membrane outline and vascular patterns were prominent. In the CNV membrane probability map obtained from CNN-M (parts C1 and C2 of FIG. 19), the regions with high probability matched well with the ground truth CNV membrane area (seen, e.g., in parts B1 and B2 of FIG. 19). Multiplying (e.g., pixel-by-pixel) the PR-OCTA outer retinal angiograms with the CNV membrane probability maps suppressed residual artifacts outside the membrane areas, which improved the reliability of CNV vessel segmentation. It is also apparent that CNN-V was able to remove the noise in the CNV inter-capillary space (part E1 of FIG. 19). The proposed techniques of this Example not only demonstrated clear CNV vasculature (part E1 of FIG. 19), but also excluded the artifacts surrounding the CNV that might be mis-segmented (e.g., part E2 of FIG. 19).

Figure 20:
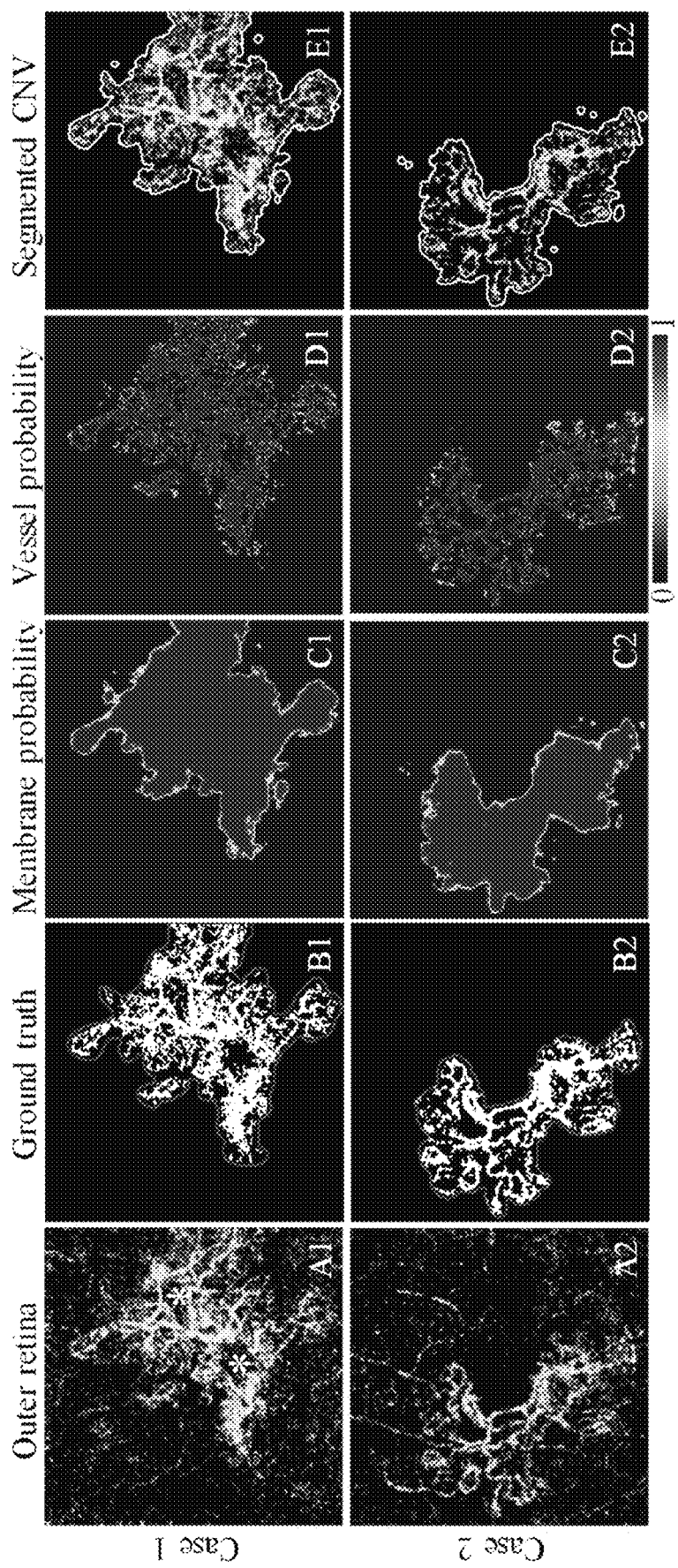
FIG. 20 illustrates CNV segmentation performed by an example CNN model on challenging scans containing a wide range of flow rates.

FIG. 20 illustrates CNV segmentation performed by the CNN model of this Example on challenging scans containing a wide range of flow rates. Parts A1 and A2 illustrate Projection-resolved (PR) outer retinal angiograms. Parts B1 and B2 illustrate manually delineated CNV membrane (red outline) and vessels (white pixels) ground truths. Parts C1 and C2 illustrate probability maps output by the (first) membrane segmentation CNN (CNN-M). Parts D1 and D2 illustrate probability maps output by the (second) vessel segmentation CNN (CNN-V). Parts E1 and E2 illustrate a segmented CNV membrane (white outline, with probability>0.5) and vessels (with pixels of probability>0.5). Large inter capillary space, highlighted by stars, were correctly included in the membrane area by the proposed algorithm.

As shown in FIG. 20, the CNN model of this Example also successfully analyzed challenging scans that previous saliency-based algorithms had difficulty correctly analyzing. One type of challenge is large CNV membrane area with wide range of flow rates (part A1 of FIG. 20). Especially in the membrane periphery, where vessels are generally smaller and have only low flow signal, the CNV area was difficult to distinguish. The saliency-based algorithm would both reject such peripheral CNV vessels (creating false negatives), and under-segment gaps in the CNV vasculature (part A1, highlighted by white stars). Using the proposed CNN model of this Example, the entire CNV membrane region showed high probability despite the influence of slow flow and large inter-capillary space (part C1), and the residual projection artifacts were also excluded in the probability map (part C2 of FIG. 20). To accomplish this, the proposed technique included utilizing the inner and outer retinal (original, slab-subtracted, and PR-OCTA) angiograms as the inputs of the first CNN, since in tandem the inner and outer retinal angiograms could indicate the location of low-flow CNV vessels that can otherwise be mistaken for projection artifacts. After excluding the residual artifacts in the PR outer retinal angiogram, the CNV vessels were further segmented with high probabilities by the second CNN.

Figure 21:
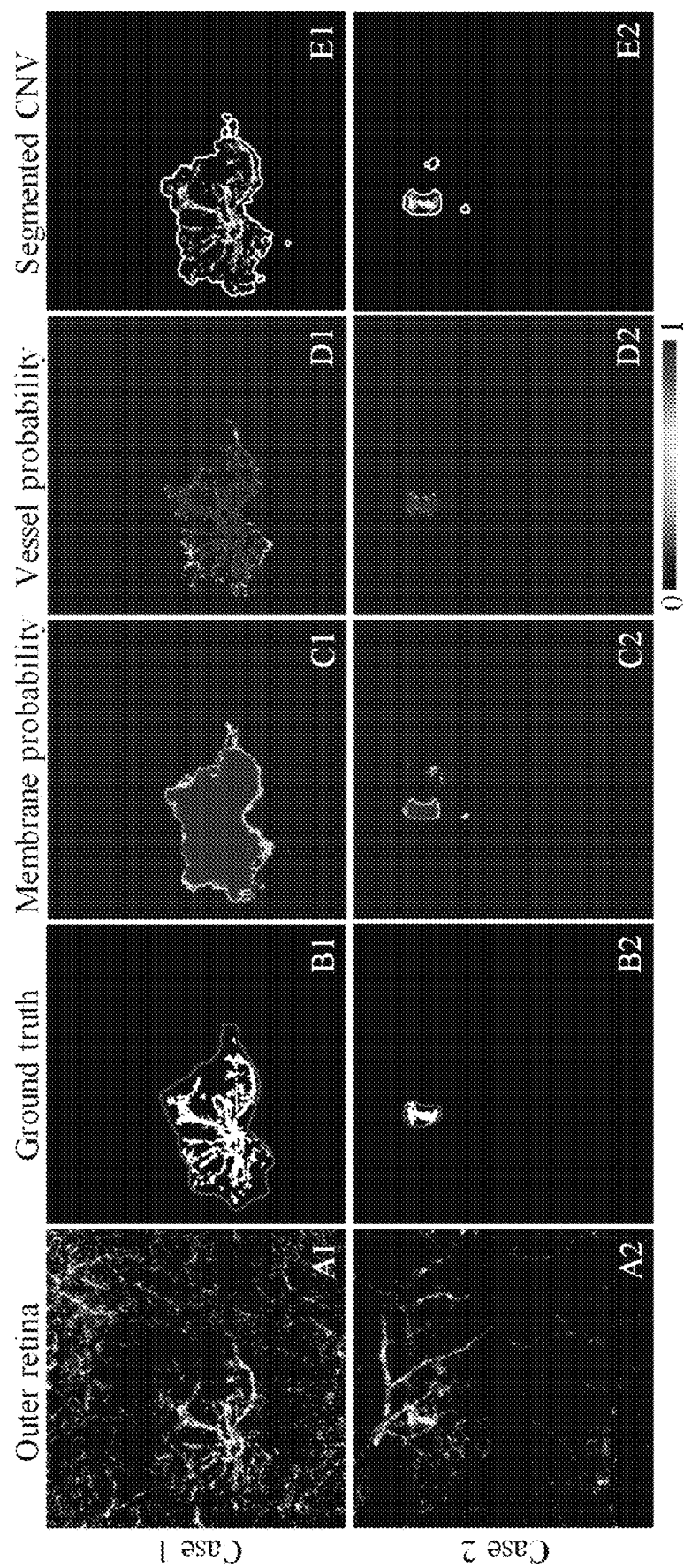
FIG. 21 illustrates an example of low flow retinas analyzed by an example CNN model.

FIG. 21 illustrates an example of obtrusive projection artifacts analyzed by the CNN model of this Example. Vessels in the CNV membrane with low flow may be faint enough to appear as projection artifacts, but in other cases projection artifacts are obtrusive enough that the projection artifacts appear as prominent as any vessels in the CNV membrane (part A1 of FIG. 21). The saliency-based algorithm would mis-segment such artifacts as true CNV (see, e.g., parts A2 and B2 of FIG. 13). The proposed CNN model described in this Example can successfully distinguish real CNV from strong residual projection artifacts in CNV cases (part A1 of FIG. 21) and a case diagnosed with retinal angiomatous proliferation (part A2 of FIG. 21), in which the neovascularization lesion lies on top of these intense residual projection artifacts since neovascularization lesion is growing from inner retina down to the outer retina. As in previous example with a large CNV membrane area, including each of the differently processed outer retinal angiograms enabled the trained network to distinguish true CNV from artifacts, since the angiographic image set and outer retinal structural volume yield features that can uniquely identify an artifact and true signal.

Figure 22:
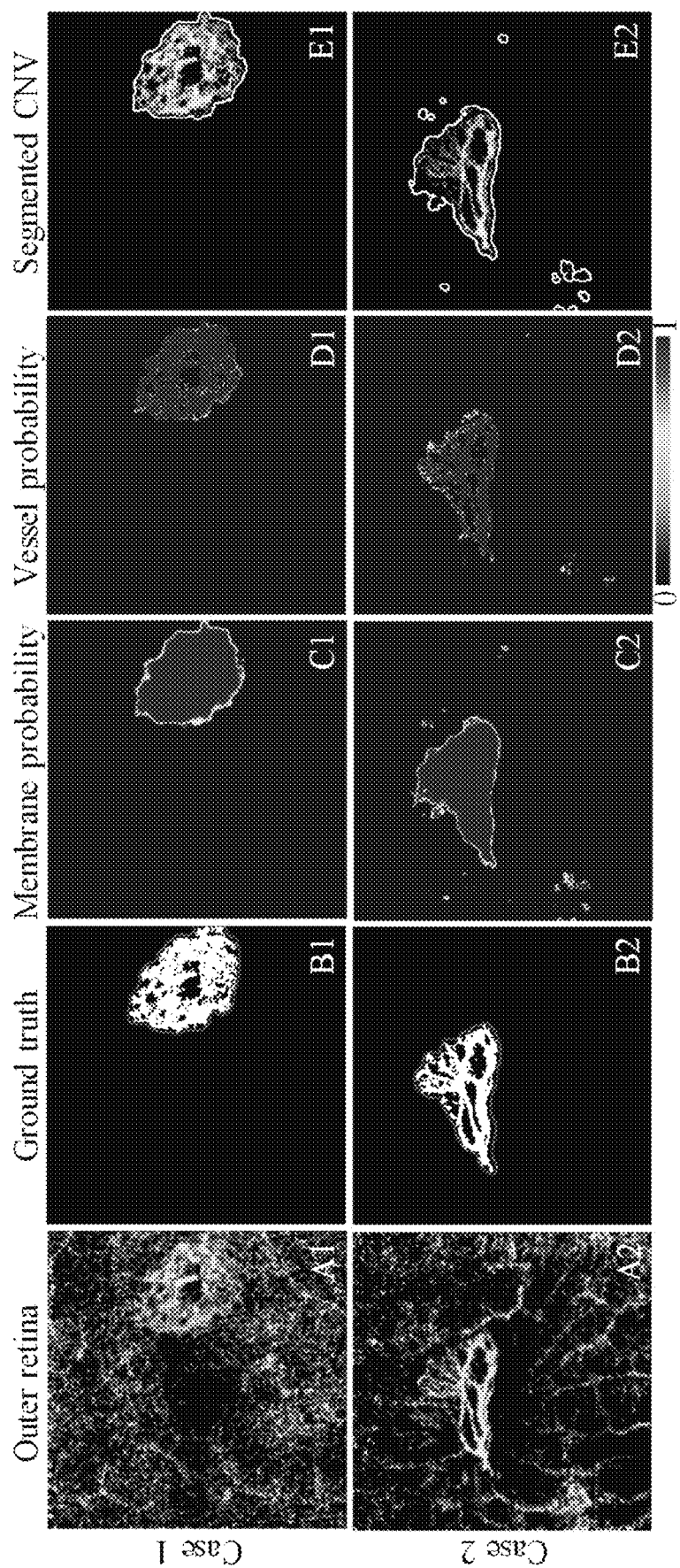
FIG. 22 illustrates an example of relatively low scan quality images analyzed by an example CNN model.

FIG. 22 illustrates an example of low scan quality images analyzed by the CNN model of this Example. Another source of difficulty for CNV analysis is low scan quality (parts A1 and A2 of FIG. 22). Two common sources of low scan quality are low signal strength and defocus. Defocus not only causes a reduction in signal strength, but also causes broadening of capillaries and generally makes images less clear (parts A1 and A2 of FIG. 22). In defocused scans, the membrane outline is consequently blurred and indistinct. Simultaneously, such low-quality scans are problematic for PR-OCTA correction, leading to more prevalent residual projection artifacts. As in the previous examples, the full angiographic image set was essential for correct exclusion of these artifacts, but as can be seen (e.g., in part C2 of FIG. 22) the first CNN (CNN-M) incorrectly segmented some projection artifacts. However, the second CNN (CNN-V) further shrank the artifacts in determining the vessel probability (e.g., in part D2 of FIG. 22), yielding a vessel segmentation that was correct despite the false positive membrane segmentations. With the benefits of CNV membrane and vessel segmentation, the visualization of the CNV on defocused scans was dramatically improved, providing an image with clear boundaries and vasculature.

One more important advantage of the proposed CNN model over the saliency-based approach is its ability to correctly omit CNV from scans in which CNV is not present. These scans are challenging because even in the absence of CNV many scans contain spurious artifactual signal. In particular, in the scans with low SSI, proprietary motion correction technology (MCT) software may fail to suppress motion artifacts after merging one X-fast and one Y-fast scan. In the saliency-based approach these artifacts would be identified as CNV (parts A4 and B4 of FIG. 13), since the artifacts appear as bright as real CNV. The artifacts also pose problems for differentiating artifact from signal using the angiographic image set used in this Example, since the artifacts do not share the same relationships between the images as projection artifacts. The inclusion of the outer retinal reflectance image is useful in such cases, since CNV development induces structural changes in the retina that can be used to differentiate afflicted eyes from either healthy eyes or eyes that have developed different pathology in outer retina. By including the reflectance information as well, the proposed CNN model was able to correctly classify eyes as CNV-free, as shown for a dry-AMD and DR case in FIG. N.

Figure 23:
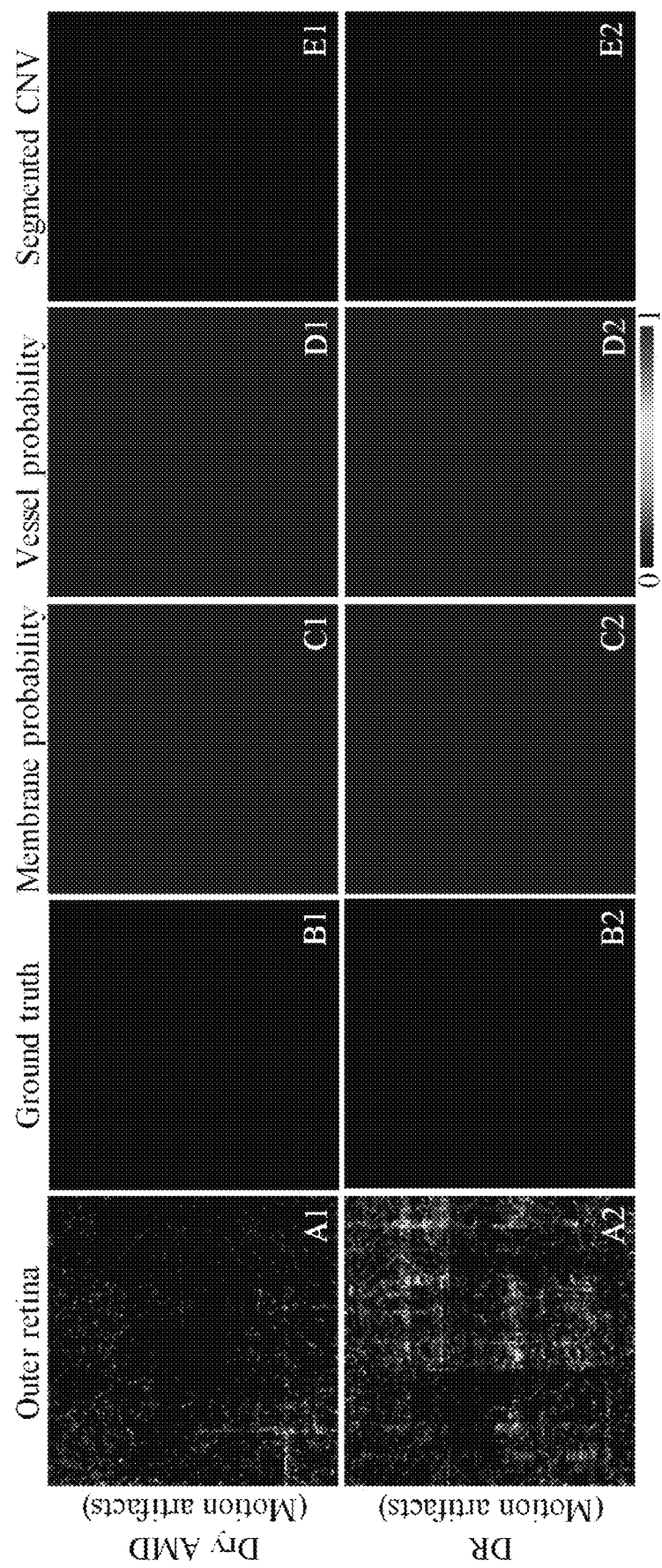
FIG. 23 illustrates that an example CNN model can correctly classify scans with no CNV present.

FIG. 23 illustrates that the CNN model of this Example can correctly classify scans with no CNV present. FIG. 23 illustrates a case with dry age-related macular degeneration (AMD; parts A1 to E1) and diabetic retinopathy (DR; parts A2 to E2). As illustrated, no CNV is delineated in ground truths (parts B1 and B2). Despite strong motion artifacts (parts A1 and A2), the probability maps produced by the CNN model (parts C1, C2, D1, and D2) did not indicate any CNV, and so the algorithm correctly does not segment any membrane or vessels in the output (parts E1 and E2). These cases are indicative of the proposed algorithm's robust performance, since CNV was not detected in either.

Discussion

This Example provides a novel technique for CNV identification and segmentation using deep learning. The CNN model described in this Example demonstrated classification based at least on whether CNV is absent or present and demonstrated segmentation of CNV membranes and vessels. Further, the CNN model demonstrated classification and segmentation on data that included both CNV scans and non-CNV scans having different pathologies, scans having high image quality, and scans having low image quality. The high sensitivity, specificity, and AROC values reported in these conditions indicate that the CNN model can achieves robust identification and segmentation.

Since CNV is a vision-threatening development in a common retinal disease, CNV has been the target of several studies seeking to use OCTA to quantify or visualize its scope. In clinical research CNV membrane areas are often drawn or segmented by manually adjusted thresholding (A. D. Treister et al., TRANSLATIONAL VISION SCIENCE & TECHNOLOGY 7, 19 (2018); M. A. Bonini Filho et al., JAMA OPHTHALMOLOGY 133, 899-906 (2015); L. Kuehlewein et al., AMERICAN JOURNAL OF OPHTHALMOLOGY 160, 739-748 (2015); M. Inoue et al., RETINA 35, 2265-2274 (2015)). However, manual segmentation is time-consuming, particularly since for accurate measurement the effect of artifacts on the OCTA visualization must be carefully considered. At the same time, automated approaches such as the saliency-based approach are readily foiled by the presence of artifacts, which are inevitable in clinical data sets (L. Liu et al., BIOMEDICAL OPTICS EXPRESS 6, 3564-3576 (2015); Y. Jia et al., OPHTHALMOLOGY 121. 1435-1444 (2014); Y. Jia et al., PNAS 201500185 (2015)). Because CNV lesions often grow from their periphery, by achieving accurate segmentation of membrane area even when the peripheral vessels are small and dim, the CNN model described herein contributes more to CNV monitoring than the performance metrics evaluated above indicate. Furthermore, previous attempts to automate CNV identification have limited their scope to just membrane segmentation. Since CNV vessel morphology is associated with CNV treatment response (P. L. Nesper et al., INVESTIGATIVE OPHTHALMOLOGY & VISUAL SCIENCE 59, 1944-1952 (2018)), vessel segmentation is also highly desirable This Example has already discussed the limitations of previous, saliency-based algorithm (L. Liu et al., BIOMEDICAL OPTICS EXPRESS 6, 3564-3576 (2015)). This Example has also previously discussed a distance mapping approach (J. Xue et al., BIOMEDICAL OPTICAL EXPRESS 9, 3208-3219 (2018)). The proposed CNN model, in common with the saliency algorithm, utilizes an intensity-based algorithm that can detect some CNV in input images and may utilize manual classification of images to determine the presence of CNV. The distance mapping method is also vulnerable to disruptions caused by projection or other artifacts. This Example has further discussed CNV segmentation performed on the slab-subtracted outer retinal angiogram (L. Liu et al., BIOMEDICAL OPTICS EXPRESS 6, 3564-3576 (2015); Y. Jia et al., OPHTHALMOLOGY 121. 1435-1444 (2014)), and Zhang et al. (A. Zhang et al., BIOMEDICAL OPTICAL EXPRESS 6, 4130-4143 (2015); Q. Zhang et al., INVESTIGATIVE OPHTHALMOLOGY & VISUAL SCIENCE 58, 1506-1513 (2017)) also proposed a morphology and edge detection-based method that relies on slab-subtraction to help mitigate the most egregious effects from projection artifacts. As noted above (See FIG. 11), CNV vascular integrity is easily damaged by slab subtraction. Finally, both of these methods, as well as previous saliency-based methods, can be trained on hand-crafted features. CNV vascular patterns contain unique features that differentiate them from noise that such approaches cannot, in general, use for segmentation (in contrast to deep learning-based approaches).

By using a varied and information-rich input data set, including outer retinal volumetric structural data and en face angiograms of the inner and outer retina with different levels and methods of error correction, the CNN model of this Example can exclude projection artifacts and noise from the CNV membrane and vessels. Several other design choices contributed to the high performance of the proposed model and method. The designed CNNs of the model utilized a modified dense network with atrous kernels in the encoder blocks. Further, the CNN model can identify features across multiple scales by increasing the atrous kernel dilation rate and parallelized feature extraction across low and high levels accelerated the training progress. It should be noted that the number of kernels can be reduced and/or kept constant to achieve a deeper network.

The techniques described in this Example accomplish the intended tasks. In particular, this Example provides a fully automated approach for CNV segmentation that can increase the amount of information available during patient monitoring and can reveal previously hidden indicators of CNV progression and prognosis. Additionally, the segmentation of vessels according to the CNN model offers additional capabilities to monitor new and potentially better CNV biomarkers in the clinic.

Example Clauses

The following clauses provide various implementations of the present disclosure.
1. A method, including: generating, by a first model based on at least one image of a retina of a subject, a membrane mask indicating a location of a CNV membrane in the retina; and generating, by a second model based on the membrane mask and the at least one image, a vasculature mask of the retina of the subject, the vasculature mask indicating CNV vascularization in the retina.
2. The method of clause 1, further including: determining that a size of the CNV membrane indicated in the membrane mask is greater than a threshold size.
3. The method of clause 1 or 2, wherein the at least one image includes at least one of a volumetric image of the retina of the subject, a volumetric image of a choroid of the subject, or a whole volume image of an eye the subject.
4. The method of any one of clauses 1 to 3, wherein the at least one image includes an inner retinal angiogram of the retina of the subject.
5. The method of any one of clauses 1 to 4, wherein the at least one image includes at least one outer retinal angiogram of the retina of the subject.
6. The method of any one of clauses 1 to 5, wherein the at least one outer retinal angiogram includes a slab-subtracted outer retinal angiogram of the retina of the subject.
7. The method of any one of clauses 1 to 6, further including: obtaining the slab-subtracted outer retinal angiogram by: obtaining a first projection image of an inner retina of the subject; obtaining a second projection image of an outer retina of the subject; and generating the slab-subtracted outer retinal angiograph by subtracting a product of the first projection image and a value from the second projection image, the value being a number between 0 and 1.
8. The method of any one of clauses 5 to 7, wherein the at least one outer retinal angiogram includes a projection-resolved outer retinal angiogram of the retina of the subject.
9. The method of any one of clauses 1 to 8, wherein the at least one image includes a volumetric structural image of an outer retina of the subject and/or a whole volumetric structural image of the retina and a choroid of the subject.
10. The method of any one of clauses 1 to 9, further including distinguishing the CNV membrane from another disease in the retina of the subject based on at least one of a structural volume image or a whole volume image of the retina of the subject.
11. The method of any one of clauses 1 to 10, wherein the location of a CNV membrane is indicated in an outer retina of the subject.
12. The method of any one of clauses 1 to 11, wherein the membrane mask indicates one or more pixels in the at least one image that have greater than a threshold probability of depicting the CNV membrane in the retina.
13. The method of any one of clauses 1 to 12, wherein the membrane mask is a binary image including pixels, a first set of the pixels having a first value and corresponding to the location of the CNV membrane in the at least one image, a second set of the pixels having a second value and corresponding to at least one non-CNV area in the at least one image.
14. The method of any one of clauses 1 to 13, wherein vasculature mask indicates one or more pixels in the at least one image that have greater than a threshold probability of depicting vessels in the CNV membrane.
15. The method of any one of clauses 1 to 14, wherein the at least one image includes first pixels and the vasculature mask is a binary image including second pixels, a first set of the second pixels having a first value and corresponding to one or more of the first pixels depicting vessels in the CNV membrane, a second set of the second pixels having a second value and corresponding to one or more of the first pixels depicting an absence of vessels in the CNV membrane.
16. The method of any one of clauses 1 to 15, further including: obtaining, by an imaging device, the at least one image.
17. The method of any one of clauses 1 to 16, further including: outputting, on a clinical device, the vasculature mask.
18. The method of any one of clauses 1 to 17, further including: outputting, on the clinical device, the membrane mask.

19. The method of any one of clauses 1 to 18, wherein the first model includes a CNN.
20. The method of clause 19, wherein generating the membrane mask includes: generating a third image based on the at least one image of the retina; generating, by a first encoder block in the CNN, a fourth image by convolving or cross-correlating the third image with a first encoder filter, the first encoder filter being associated with a first kernel dilation rate; generating, by a second encoder block in the CNN, a fifth image by convolving or cross-correlating the fourth image with a second encoder filter, the second encoder filter being associated with a second kernel dilation rate; generating, by a decoder block in the CNN, a sixth image by concatenating the fourth image and the fifth image; generating, by the decoder block, a seventh image by convolving or cross-correlating the fifth image with a decoder filter without dilation; and generating the membrane mask based on the seventh image.
21. The method of clause 20, wherein the first kernel dilation rate is a first atrous kernel dilation rate and the second kernel dilation rate is a second atrous kernel dilation rate.
22. The method of any one of clauses 1 to 21, wherein the at least one image includes a structural volume image of the retina and at least one angiographic image of the retina, and wherein generating the membrane mask includes: generating an input image by concatenating the structural volume image and the at least on angiographic image; generating, by the CNN, an output image by performing at least one of a convolution operation, a cross-correlation operation, or a concatenation operation on the input image; generating a probability map by performing parallelized multi-scale feature extraction on the output image; and generating the membrane mask by applying a softmax and/or a sigmoid activation function to the probability map.
23. The method of any one of clauses 20 to 22, the subject being a first subject and the retina being a first retina, the method further including: generating the first model by training the CNN using a plurality of training images, the training images including: third images of second retinas of second subjects, the second subjects omitting the first subject; and manually segmented CNV maps of the third images.
24. The method of any one of clauses 1 to 23, wherein the second model includes a CNN.
25. The method of 24, wherein generating the vasculature mask includes: generating a third image based on the membrane mask and the at least one image of the retina; generating, by a first encoder block in the CNN, a fourth image by convolving or cross-correlating the third image with a first encoder filter, the first encoder being associated with a first kernel dilation rate; generating, by a second encoder block in the CNN, a fifth image by convolving or cross-correlating the fourth image with a second encoder filter, the second encoder filter being associated with a second kernel dilation rate; generating, by a decoder block in the CNN, a sixth image by concatenating the fourth image and the fifth image; generating, by the decoder block, a seventh image by convolving or cross-correlating the fifth image with a decoder filter without dilation; and generating the vasculature mask based on the seventh image.
26. The method of clause 25, wherein the first kernel dilation rate is a first atrous kernel dilation rate and the second dilation rate is a second atrous kernel dilation rate.
27. The method of any one of clauses 24 to 26, wherein the at least one image includes a structural volumetric image of the retina and at least one angiographic image of the retina, and wherein generating the vasculature mask includes: generating at least one third image by convolving the at least one first angiographic image with the membrane mask; generating a fourth image by concatenating the at least one third image with the structural volume image; generating, by the CNN, a fifth image by performing at least one of a convolution operation, a cross-correlation operation, or a concatenation operation on the fourth image; generating a sixth image by performing parallelized multi-scale feature extraction on the fifth image; and generating the vasculature mask by performing softmax activation on the sixth image.
28. The method of any one of clauses 24 to 27, the subject being a first subject and the retina being a first retina, the method further including: generating the second model by training the CNN using a plurality of training images, the training images including: third images of second retinas of second subjects, the second subjects omitting the first subject; and manually segmented membrane masks and vasculature masks of the third images.
29. A system, including: at least one processor; and memory storing instructions that, when executed by the at least one processor, cause the at least one processor to perform operations including any one of methods 1 to 28.
30. The system of clause 29, further including an imaging device configured to generate the at least one image.
31. The system of clause 30, wherein the imaging device includes an OCT imaging device.
32. The system of clause 29, further including: a device configured to display at least one of the membrane mask or the vasculature mask.
33. A non-transitory computer-readable medium including instructions to perform operations including any one of the methods recited in clauses 1 to 28.
34. A system, including: at least one processor; and memory storing instructions that, when executed by the at least one processor, cause the at least one processor to perform: a first model configured to generate, based on at least one image of a retina of a subject, a membrane mask indicating a first location of a CNV membrane in the retina; and a second model configured to generate, based on the membrane mask and the at least one image, a vasculature mask of indicating a second location of at least one vessel in the CNV membrane.
35. The system of clause 34, further including: an OCT imaging device configured to capture the at least one image of the retina.
36. The system of clause 34 or 35, wherein the first model includes blocks arranged in series, wherein the blocks include: a first encoder block configured to generate a first output by performing first operations on an input, the input being based on the at least one image of the retina, the first operations including at least one first convolution operation; a second encoder block configured to generate a second output by performing second operations on the first input, the second operations including at least one second convolution operation; a decoder block configured to generate a third output by: generating a combined output by concatenating the first output and the second output; and performing third operations on the combined output, the third operations including at least one third convolution operation.
37. The system of clause 36, wherein the at least one first convolution operation includes a first atrous convolution operation associated with a first dilation rate and the at least one second convolution operation includes a second atrous convolution operation associated with a second dilation rate, the second dilation rate being greater than the first dilation rate.
38. The system of clause 37, wherein the third convolution operation is performed without dilation.
39. The system of any one of clauses 36 to 38, wherein the first encoder block includes: a first convolution block configured to generate a fourth output by performing a fourth convolution operation on the input; a concatenation layer configured to generate a fifth output by performing a concatenation operation on the input and the fourth output; and a second convolution block configured to generate a sixth output by performing a fifth convolution operation on the fifth output, wherein the second output is based on the fifth output.
40. The system of any one of clauses 36 to 39, wherein the input is a first input, and the blocks further include: a parallelized multi-scale feature extraction block including: convolution blocks configured to generate, respectively, fourth outputs by performing fourth convolution operations on a second input, the second input being based on the third output, the convolution blocks being associated with different dilation rates; and a concatenation layer configured to generate a fifth output by concatenating the fourth outputs, wherein the membrane mask is based on the fifth output.
41. The system of any one of clauses 34 to 40, wherein the second model includes blocks arranged in series, wherein the blocks include: a combination function configured to generate an input by combining the membrane mask and the at least one image; a first encoder block configured to generate a first output by performing first operations on the input, the first operations including at least one first convolution operation; a second encoder block configured to generate a second output by performing second operations on the first output, the second operations including at least one second convolution operation; a decoder block configured to generate a third output by: generating a combined output by concatenating the first output and the second output; and performing third operations on the combined output, the third operations including at least one third convolution operation.
42. The system of clause 41, wherein the at least one first convolution operation includes a first atrous convolution operation associated with a first dilation rate and the at least one second convolution operation includes a second atrous convolution operation associated with a second dilation rate, the second dilation rate being greater than the first dilation rate.
43. The system of clause 42, wherein the third convolution operation is performed without dilation.
44. The system of any one of clauses 41 to 43, wherein the first encoder block includes:
45. a first convolution block configured to generate a fourth output by performing a fourth convolution operation on the input; a concatenation layer configured to generate a fifth output by performing a concatenation operation on the input and the fourth output; and a second convolution block configured to generate a sixth output by performing a fifth convolution operation on the fifth output, wherein the second output is based on the fifth output.
46. The system of any one of clauses 40 to 45, wherein the input is a first input, and the blocks further include: a parallelized multi-scale feature extraction block including: convolution blocks configured to generate, respectively, fourth outputs by performing fourth convolution operations on a second input, the second input being based on the third output, the convolution blocks being associated with different dilation rates; and a concatenation layer configured to generate a fifth output by concatenating the fourth outputs, wherein the vasculature mask is based on the fifth output.
47. The system of any one of clauses 34 to 46, further including: a device configured to display the at least one image of the retina, the membrane mask, and the vasculature mask.

CONCLUSION

The environments and individual elements described herein may of course include many other logical, programmatic, and physical components, of which those shown in the accompanying figures are merely examples that are related to the discussion herein.

Other architectures may be used to implement the described functionality and are intended to be within the scope of this disclosure. Furthermore, although specific distributions of responsibilities are defined above for purposes of discussion, the various functions and responsibilities might be distributed and divided in different ways, depending on circumstances.

Furthermore, although the subject matter has been described in language specific to structural features and/or methodological acts, it is to be understood that the subject matter defined in the appended claims is not necessarily limited to the specific features or acts described. Rather, the specific features and acts are disclosed as exemplary forms of implementing the claims.

As will be understood by one of ordinary skill in the art, each embodiment disclosed herein can comprise, consist essentially of, or consist of its particular stated element(s), step(s), ingredient(s), and/or component(s). Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiments. In the current context, a material affect includes accurately identifying position(s) of at least one CNV vascular area within 0.1 mm.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventors expect skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

It is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Explicit definitions and explanations used in the present disclosure are meant and intended to be controlling in any future construction unless clearly and unambiguously modified in examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. A medical device comprising:
   an imaging device configured to generate at least one image of a retina of a subject by performing a projection-resolved optical coherence tomographic angiography (PR-OCTA) scan on the retina of the subject;
   at least one processor;
   memory storing instructions that, when executed by the at least one processor, cause the at least one processor to perform operations comprising:
      generating, by a first model based on the at least one image of the retina of the subject, a membrane mask indicating a location of a choroidal neovascularization (CNV) membrane in the retina;
      determining that a size of the CNV membrane indicated in the membrane mask is greater than a threshold size; and
      generating, by a second model based on the membrane mask and the at least one image, a vasculature mask of the retina of the subject, the vasculature mask indicating CNV vascularization in the retina; and a display device configured to display at least one of the membrane mask or the vasculature mask.

2. The medical device of claim 1, wherein the first model comprises a convolutional neural network (CNN), and
wherein generating the membrane mask comprises:
generating a first generated image based on the at least one image of the retina;
generating, by a first encoder block in the CNN, a second generated image by convolving or cross-correlating the first generated image with a first encoder filter, the first encoder filter being associated with a first atrous kernel dilation rate;
generating, by a second encoder block in the CNN, a third generated image by convolving or cross-correlating the second generated image with a second encoder filter, the second encoder filter being associated with a second atrous kernel dilation rate;
generating, by a decoder block in the CNN, a fourth generated image by concatenating the second generated image and the third generated image;
generating, by the decoder block, a fifth generated image by convolving or cross-correlating the fourth generated image with a decoder filter without dilation; and
generating the membrane mask based on the fifth generated image.

3. The medical device of claim 1, wherein the second model comprises a convolutional neural network (CNN), and
wherein generating the vasculature mask comprises:
generating a first generated image by combining the membrane mask and the at least one image of the retina;
generating, by a first encoder block in the CNN, a second generated image by convolving or cross-correlating the first generated image with a first encoder filter, the first encoder being associated with a first atrous kernel dilation rate;
generating, by a second encoder block in the CNN, a third generated image by convolving or cross-correlating the second generated image with a second encoder filter, the second encoder filter being associated with a second atrous kernel dilation rate;
generating, by a decoder block in the CNN, a fourth generated image by concatenating the second generated image and the third generated image;
generating, by the decoder block, a fifth generated image by convolving or cross-correlating the fourth generated image with a decoder filter without dilation; and
generating the vasculature mask based on the fifth generated image.

4. A method, comprising:
generating, by a first model based on at least one image of a retina of a subject, a membrane mask indicating a location of a a choroidal neovascularization (CNV) membrane in the retina; and
generating, by a second model based on the membrane mask and the at least one image, a vasculature mask of the retina of the subject, the vasculature mask indicating CNV vascularization in the retina.

5. The method of claim 4, wherein the at least one image comprises at least one of a volumetric image of the retina of the subject, a volumetric image of a choroid of the subject, a whole volume image of an eye the subject, an inner retinal angiogram of the retina of the subject, a slab-subtracted outer retinal angiogram of the retina of the subject, or a projection-resolved outer retinal angiogram of the retina of the subject.

6. The method of claim 5, further comprising:
obtaining the slab-subtracted outer retinal angiogram by:
obtaining a first projection image of an inner retina of the subject;
obtaining a second projection image of an outer retina of the subject; and
generating the slab-subtracted outer retinal angiograph by subtracting a product of the first projection image and a value from the second projection image, the value being a number between 0 and 1.

7. The method of claim 4, wherein the at least one image comprises first pixels and the vasculature mask comprises second pixels, a first set of the second pixels having a first value and corresponding to one or more of the first pixels that have greater than a threshold probability of depicting vessels in the CNV membrane, a second set of the second pixels having a second value and corresponding to one or more of the first pixels depicting an absence of vessels in the CNV membrane.

8. The method of claim 4, wherein the first model comprises a convolutional neural network (CNN), and wherein generating the membrane mask comprises:
generating a first generated image based on the at least one image of the retina;
generating, by a first encoder block in the CNN, a second generated image by convolving or cross-correlating the first generated image with a first encoder filter, the first encoder filter being associated with a first kernel dilation rate;
generating, by a second encoder block in the CNN, a third generated image by convolving or cross-correlating the second generated image with a second encoder filter, the second encoder filter being associated with a second kernel dilation rate;
generating, by a decoder block in the CNN, a fourth generated image by concatenating the second generated image and the third generated image;
generating, by the decoder block, a fifth generated image by convolving or cross-correlating the fourth generated image with a decoder filter without dilation; and
generating the membrane mask based on the fifth generated image.

9. The method of claim 4, wherein the first model comprises a CNN,
wherein the at least one image comprises a structural volume image of the retina and at least one angiographic image of the retina, and
wherein generating the membrane mask comprises:
generating an input image by concatenating the structural volume image and the at least on angiographic image;
generating, by the CNN, an output image by performing at least one of a convolution operation, a cross-correlation operation, or a concatenation operation on the input image;
generating a probability map by performing parallelized multi-scale feature extraction on the output image; and
generating the membrane mask by applying at least one of a softmax or a sigmoid activation function to the probability map.

10. The method of claim 4, wherein the second model comprises a convolutional neural network (CNN), and
wherein generating the vasculature mask comprises:
generating a first generated image based on the membrane mask and the at least one image of the retina;
generating, by a first encoder block in the CNN, a second generated image by convolving or cross-correlating the first generated image with a first encoder filter, the first encoder being associated with a first kernel dilation rate;
generating, by a second encoder block in the CNN, a third generated image by convolving or cross-correlating the second generated image with a second encoder filter, the second encoder filter being associated with a second kernel dilation rate;
generating, by a decoder block in the CNN, a fourth generated image by concatenating the second generated image and the third generated image;
generating, by the decoder block, a fifth generated image by convolving or cross-correlating the fourth generated image with a decoder filter without dilation; and
generating the vasculature mask based on the fifth generated image.

11. The method of claim 4, wherein the second model comprises a convolutional neural network (CNN),
wherein the at least one image comprises a structural volumetric image of the retina and at least one angiographic image of the retina, and
wherein generating the vasculature mask comprises:
generating at least one first generated image by convolving the at least one angiographic image with the membrane mask;
generating a second generated image by concatenating the at least one first generated image with the structural volume image;
generating, by the CNN, a third generated image by performing at least one of a convolution operation, a cross-correlation operation, or a concatenation operation on the second generated image;
generating a fourth generated image by performing parallelized multi-scale feature extraction on the third generated image; and
generating the vasculature mask by performing softmax activation on the fourth generated image.

12. A system, comprising:
at least one processor; and
memory storing instructions that, when executed by the at least one processor, cause the at least one processor to perform:
a first model configured to generate, based on at least one image of a retina of a subject, a membrane mask indicating a first location of a a choroidal neovascularization (CNV) membrane in the retina; and
a second model configured to generate, based on the membrane mask and the at least one image, a vasculature mask of indicating a second location of at least one vessel in the CNV membrane.

13. The system of claim 12, further comprising:
an optical coherence tomography (OCT) imaging device configured to capture the at least one image of the retina by performing a projection-resolved optical coherence tomography angiography (PR-OCTA) scan on the retina.

14. The system of claim 12, wherein the first model comprises blocks arranged in series, wherein the blocks comprise:

a first encoder block configured to generate a first output by performing first operations on an input, the input being based on the at least one image of the retina, the first operations comprising at least one first convolution operation;
a second encoder block configured to generate a second output by performing second operations on the first input, the second operations comprising at least one second convolution operation;
a decoder block configured to generate a third output by:
generating a combined output by concatenating the first output and the second output; and
performing third operations on the combined output, the third operations comprising at least one third convolution operation.

15. The system of claim 14, wherein the at least one first convolution operation comprises a first atrous convolution operation associated with a first dilation rate and the at least one second convolution operation comprises a second atrous convolution operation associated with a second dilation rate, the second dilation rate being greater than the first dilation rate, and
wherein the third convolution operation is performed without dilation.

16. The system of claim 14, wherein the first encoder block comprises:
a first convolution block configured to generate a fourth output by performing a fourth convolution operation on the input;
a concatenation layer configured to generate a fifth output by performing a concatenation operation on the input and the fourth output; and
a second convolution block configured to generate a sixth output by performing a fifth convolution operation on the fifth output, and
wherein the second output is based on the fifth output.

17. The system of claim 14, wherein the input is a first input, and the blocks further comprise:
a parallelized multi-scale feature extraction block comprising:
convolution blocks configured to generate, respectively, fourth outputs by performing fourth convolution operations on a second input, the second input being based on the third output, the convolution blocks being associated with different dilation rates; and
a concatenation layer configured to generate a fifth output by concatenating the fourth outputs, and
wherein the membrane mask is based on the fifth output.

18. The system of claim 12, wherein the second model comprises blocks arranged in series, wherein the blocks comprise:
a combination function configured to generate an input by combining the membrane mask and the at least one image of the retina of the subject;
a first encoder block configured to generate a first output by performing first operations on the input, the first operations comprising at least one first convolution operation;
a second encoder block configured to generate a second output by performing second operations on the first output, the second operations comprising at least one second convolution operation;
a decoder block configured to generate a third output by:
generating a combined output by concatenating the first output and the second output; and performing third operations on the combined output, the third operations comprising at least one third convolution operation, wherein the at least one first convolution operation comprises a first atrous convolution operation associated with a first dilation rate and the at least one second convolution operation comprises a second atrous convolution operation associated with a second dilation rate, the second dilation rate being greater than the first dilation rate, and wherein the third convolution operation is performed without dilation.

19. The system of claim 18, wherein the first encoder block comprises:
a first convolution block configured to generate a fourth output by performing a fourth convolution operation on the input;
a concatenation layer configured to generate a fifth output by performing a concatenation operation on the input and the fourth output; and
a second convolution block configured to generate a sixth output by performing a fifth convolution operation on the fifth output, and wherein the second output is based on the fifth output.

20. The system of claim 18, wherein the input is a first input, and the blocks further comprise:
a parallelized multi-scale feature extraction block comprising:
convolution blocks configured to generate, respectively, fourth outputs by performing fourth convolution operations on a second input, the second input being based on the third output, the convolution blocks being associated with different dilation rates; and
a concatenation layer configured to generate a fifth output by concatenating the fourth outputs, and wherein the vasculature mask is based on the fifth output.

* * * * *